(12) United States Patent
Chhabra et al.

(10) Patent No.: US 6,500,459 B1
(45) Date of Patent: Dec. 31, 2002

(54) CONTROLLED ONSET AND SUSTAINED RELEASE DOSAGE FORMS AND THE PREPARATION THEREOF

(76) Inventors: Harinderpal Chhabra, 10-Landing La., Apt. #9F, New Brunswick, NJ (US) 08901; Shyamal K. Sarkar, 7-Pineglen Dr., Blauvelt, NY (US) 10913-1150

(*) Notice: Subject to any disclaimer, the term of this patent is extended or adjusted under 35 U.S.C. 154(b) by 0 days.

(21) Appl. No.: 09/358,732

(22) Filed: Jul. 21, 1999

(51) Int. Cl.⁷ .............................. A61K 9/22; A61K 9/24; A61K 9/30
(52) U.S. Cl. .................. 424/474; 424/468; 424/470; 424/472; 424/475; 514/770; 514/772.3; 514/777; 514/778; 514/779; 514/780; 514/781; 514/782
(58) Field of Search .................. 424/468, 469, 424/470, 472, 474, 475, 479, 480

(56) References Cited

U.S. PATENT DOCUMENTS 5,690,960 A * 11/1997 Bengtsson et al. .......... 424/480

* cited by examiner

Primary Examiner—James M. Spear
(74) Attorney, Agent, or Firm—Kitt Sinden; Marcelo K. Sarkis; Ivor M. Hughes

(57) ABSTRACT

A pharmaceutical composition for controlled onset and sustained release of an active ingredient, said composition comprising:
(i) a core comprising:
(a) an active ingredient;
(b) a hydrophilic carrier;
(c) a hydrodynamic diffusion enhancer; and optionally
(d) conventional pharmaceutically acceptable excipients selected from the group consisting of binders, fillers and lubricants and combinations thereof; and
(ii) a functional coating membrane surrounding said core.

46 Claims, 7 Drawing Sheets

Effect of % wt. Gain in coating on release rates

| Time | 3% Aquacoat | 4.5% Aquacoat | 4% Aquacoat |
|---|---|---|---|
| 0 | 0 | 0 | 0 |
| 1 | 1.06 | 0 | 0.31 |
| 2 | 3.31 | 0.76 | 1.2 |
| 3 | 10.7 | 3.96 | 5.95 |
| 4 | 20.7 | 8.86 | 12.95 |
| 6 | 40.9 | 19.46 | 27.43 |
| 8 | #N/A | 32.13 | 44.47 |
| 9 | 73.8 | #N/A | #N/A |
| 10 | #N/A | 42.66 | 60.71 |
| 11 | 87.2 | #N/A | #N/A |
| 12 | #N/A | #N/A | #N/A |
| 13 | 109.4 | 61.1 | 82.22 |
| 14 | #N/A | #N/A | #N/A |
| 15 | #N/A | #N/A | #N/A |
| 16 | 109.9 | 79.74 | 102.07 |
| 22 | #N/A | #N/A | #N/A |
| 24 | 114 | 103.88 | 111.563 |

Effect of % wt. Gain in coating on the release profile of glipizide

CONTROLLED ONSET AND SUSTAINED RELEASE DOSAGE FORMS AND THE PREPARATION THEREOF

FIELD OF THE INVENTION

The present invention relates to dosage forms for controlled onset and sustained release of active ingredients for human or animal use.

BACKGROUND OF THE INVENTION

The goal of any drug delivery system is to provide an effective therapeutic amount of a drug to a targeted site in the body to obtain quickly, and then maintain, the desired drug concentration. The two most important aspects of drug delivery are spatial placement and temporal delivery of a drug. Spatial placement relates to the targeting of a drug to a specific organ or tissue, while temporal delivery refers to controlling the rate of drug delivery to the target tissue.

Sustained release drug delivery systems are designed in an attempt to satisfy the spatial placement and temporal delivery of a drug. Sustained release drug delivery systems include any drug delivery system that achieves slow release of a drug over an extended period of time. If these sustained release drug delivery systems can provide some control of drug release in the body, whether this be of a temporal or spatial nature, or both, or in other words, the system is successful at maintaining constant drug levels in the target tissue or cells, it is considered to be a controlled release drug delivery system.

Some therapeutic programs require that the dose of a drug be administered in a time varying pattern of delivery such as a drug free interval followed by a sustained release of the drug for an extended period of time. The science of chronotherapeutics relies on the practice of delivering an effective therapeutic amount of a drug to the desired site of action at the most appropriate time period for a particular disease condition. For example, the greatest incidence of cardiovascular disorders including angina, stroke, heart attack, etc., typically occur during the early morning hours when blood pressure is rising in response to an animal's natural circadian rhythm. This rise in blood pressure, which occurs at waking, requires a dosage form that is administered upon retiring which dosage form delivers its drug before waking but after a drug free interval during sleep. This time varying pattern or controlled onset of drug delivery provides the required therapy at the appropriate time, thereby substantially lessening the instance of a waking elevated blood pressure.

It is well known in the prior art to provide dosage forms that deliver their contents at a desired rate after a predetermined time delay. Applicant is aware of two such controlled onset and sustained release drug delivery systems currently on the market namely, Verelan® PM by Schwarz Pharma and Covera-HS™ by G.D. Searle & Co. Verelan® PM is a verapamil hydrochloride capsule formulation utilizing the proprietary CODAS™ (Chronotherapeutic Oral Drug Absorption System) technology, developed by Elan Corporation PLC and which technology is based on U.S. Pat. No. 4,863,742. U.S. Pat. No. 4,863,742 relates to a controlled absorption verapamil containing pellet formulation for oral administration comprising: (i) a core of (a) a powder mixture containing verapamil or a salt thereof and an organic acid, and (b) a polymeric material containing a major proportion of a water soluble polymer and a minor proportion of a water insoluble polymer, the core comprising layers of the powder mixture and the polymeric material superimposed one upon the other; and (ii) a multi-layer membrane surrounding the core and containing a major proportion of a film-forming, water insoluble polymer and a minor proportion of a film forming water soluble polymer; the release of the verapamil from the pellet being substantially independent of pH and at a rate allowing controlled absorption thereof over a 24 hour period following oral administration.

The individual pellets formulated according to U.S. Pat. No. 4,863,742 may be filled into hard or soft gelatin capsules or may be compressed into tablets. The pellets in the formulation may consist of a blend of pellets formulated to provide various release rates of verapamil. Upon ingestion, the hard or soft gelatin capsules dissolve immediately, thus releasing the individual pellets into the gastrointestinal tract. Likewise, upon ingestion, the compressed tablets are designed to fall apart immediately, thus releasing the individual pellets into the gastrointestinal tract.

The Verelan® PM capsule formulation, which is based on the teachings of U.S. Pat. No. 4,863,742, is a controlled onset sustained release drug delivery system designed for bed time administration, which incorporates a 4 to 5 hour delay in drug delivery. The Verelan® PM capsule formulation initiates the release of verapamil hydrochloride 4 to 5 hours after ingestion and results in a maximum plasma concentration ($C_{max}$) of verapamil hydrochloride in the morning hours. The pellet filled, hard gelatin capsules provide for extended release of verapamil hydrochloride in the gastrointestinal tract. The delay is introduced by the level of non-enteric release controlling polymer applied to the verapamil hydrochloride loaded beads. The release controlling polymer is a combination of water soluble and water insoluble polymers. As water from the gastrointestinal tract comes into contact with the polymer coated beads, the water soluble polymer slowly dissolves and the verapamil hydrochloride diffuses through the resulting pores in the coating. The water insoluble polymer continues to act as a barrier, maintaining the controlled release of the verapamil hydrochloride. The rate of release is essentially independent of pH, posture, and gastrointestinal motility in fed or fasting conditions.

The formulation disclosed in U.S. Pat. No. 4,863,742 and thus the currently marketed Verelan® PM capsule formulation, has several limitations. In the acidic environment of the stomach (pH 1 to 3) where the verapamil is water soluble, the gastric fluid diffuses through the permeable membrane of each pellet, dissolves the verapamil, and diffuses out through the permeable membrane of each pellet with the dissolved verapamil. The purpose of the organic acid is purportedly to maintain an acidic micro-environment in the pellet core to keep the verapamil soluble, even when the pellet is introduced into the alkaline environment of the lower gastrointestinal tract. Thus, when the pellets descend through the stomach into the alkaline environment of the lower gastrointestinal tract (pH 5 to 7), the verapamil purportedly continues to be dissolved because of the purported continued presence of the organic acid in the core which organic acid maintains the acidity of the micro-environment (assuming the acid has not diffused out). Fluid entering the pellet from the lower gastrointestinal tract (even though more basic) is purportedly neutralized by the presence of the organic acid and the relatively low pH maintained so that the verapamil can purportedly remain in its more soluble state in the maintained acidic micro-environment. Thus, the verapamil purportedly continues to dissolve and diffuse through the multi-layer permeable membrane into the lower gastrointestinal tract.

The difficulty of the approach used in the formulation disclosed in U.S. Pat. No. 4,863,742 and thus the approach used in the Verelan® PM capsule formulation, is two-fold. Firstly, the organic acid is soluble. Therefore, the organic acid dissolves and diffuses out from the core through the multi-layer permeable membrane as the pellets pass through the gastrointestinal tract. Secondly, the organic acid is subject to neutralization as a result of its contact with the alkaline environment of the lower gastrointestinal tract, where the effectiveness of the organic acid is most needed. At the time when only a percentage of the original amount of verapamil is present in the core, there is a stronger need for solubilization because the less product inside the core, the higher the osmotic pressure needed to permit the verapamil to be pushed out. However, at that point, the quantity of organic acid has had time to diffuse out and another quantity of organic acid has had time to be neutralized. Thus, the organic acid concentration is lower and the system loses its ability to adequately acidify the micro-environment within the pellet surrounded by the multi-layer permeable membrane, becoming less effective when it is more and more needed. As a result of this phenomena, the pellets formulated in accordance with U.S. Pat. No. 4,863,742 and thus the Verelan® PM capsule formulation does not reliably release verapamil at a sustained rate.

Covera-HS™ is a verapamil hydrochloride tablet formulation utilizing the proprietary OROS® (Oral Osmotic) technology developed by Alza Corporation and which technology is based on U.S. Pat. Nos. 5,160,744; 5,190,765; and 5,252,338. U.S. Pat. No. 5,160,744 relates to a dosage form for the delayed-delivery of a drug, wherein the dosage form comprises: (a) a first composition comprising the drug verapamil and a poly(ethylene oxide), said poly(ethylene oxide) comprising means for changing from a nondispensable viscosity to a dispensable viscosity when contacted by fluid that enters the dosage form; (b) a second composition comprising a polymeric composition that imbibes fluid and expands, whereby the second composition pushes the first composition from the dosage form; (c) a wall that surrounds the first and second compositions, said wall permeable to the passage of fluid present in the environment of use and comprises a polymeric composition that hydrates slowly when contacted by fluid that enters the wall; (d) at least one exit mans in the wall for delivering the drug from the dosage form; and, wherein the dosage form is characterized by: (e) a delayed-drug interval for delivering verapamil up to 4.5 hours provided by (a), (b) and (c) operating in combination as a unit to provide the delayed-drug interval.

U.S. Pat. Nos. 5,190,765 and 5,252,338 relate to a dosage form for the delayed-delivery of a drug to a fluid environment of use, wherein the dosage form comprises: (a) drug composition comprising a calcium channel blocker drug, and a polymer comprising a molecular weight up to 1,000,000 and a rate of hydration in the presence of fluid that enters the dosage form to change from a non-dispensable phase to a dispensable phase; (b) a push composition that imbibes fluid and expands, whereby the push composition pushes the calcium channel blocker drug composition from the dosage form; (c) a wall that surrounds the drug and push compositions, said wall comprising a semi-permeable cellulose polymer composition permeable to the passage of fluid present in the environment of use, and a different cellulose polymer comprising a 8,500 to 4,000,000 molecular weight for slowing the rate of fluid passage through the semi-permeable cellulose polymer composition of the wall; (d) at least one exit means in the wall for delivering the drug from the dosage form; and wherein the dosage form is characterized by: (e) a subcoat for the delayed-delivery of drug, which subcoat comprises a hydroxyalkylcellulose polymer possessing a 8,500 to 4,000,000 molecular weight that surrounds the drug and push composition and is positioned between the inside surface of the wall and the drug and push composition; and characterized further by: (f) a delayed-delivery of 30 minutes to 7 hours is provided by (1) the polymer in the drug composition, (2) the polymer in the wall composition and (3) the polymer in the subcoat operating in conjunction, whereby through the combined operations of (1), (2) and (3) a delayed-delivery of the calcium channel blocker drug is provided by the dosage form.

U.S. Pat. Nos. 5,160,744; 5,190,765; and 5,252,338 all relate generally to dosage forms for the controlled drug delivery of a drug, wherein osmotic pressure is employed as the driving force to generate a constant release of the drug from the dosage form provided a constant osmotic pressure is maintained. The dosage forms comprise a semi-permeable membrane, permeable to the passage of exterior fluid and substantially impermeable to the passage of drug, the semi-permeable membrane surrounding and forming a compartment comprising a drug layer and an osmotic layer and, at least one preformed passageway in the membrane communicating with the drug layer in the compartment and the exterior of the dosage form. Typical materials for forming the semi-permeable membrane are cellulose esters, cellulose ethers and cellulose ester-ethers. When the dosage form is exposed to water or any fluid in the body, water is imbibed into the dosage form in a tendency towards osmotic equilibrium due to the osmotic pressure difference. The volume flow rate of water into the dosage form is determined by the osmotic pressure gradient across the membrane and the permeability, area and thickness of the membrane. The drug is pumped out of the dosage form through the orifice at a controlled rate, the rate of which is determined by the volume flow rate of water into the dosage form and the concentration of the drug inside the dosage form.

The Covera-HS™ tablet formulation, which is based on the teachings of U.S. Pat. Nos. 5,160,744; 5,190,765; and 5,252,338, is a controlled onset sustained release drug delivery system designed for bedtime dosing, incorporating a 4 to 5-hour delay in drug delivery. The Covera-HS™ tablet formulation initiates the release of verapamil hydrochloride 4 to 5 hours after ingestion and results in a maximum plasma concentration ($C_{max}$) of verapamil hydrochloride in the morning hours. The delay is introduced by a layer between the active drug core and the outer semi-permeable membrane. As water from the gastrointestinal tract enters the tablet, the delay coating is solubilized and released. As tablet hydration continues, the osmotic layer expands and pushes against the drug layer, releasing verapamil hydrochloride through precision laser drilled orifices in the outer membrane at a constant rate. This controlled rate of drug delivery in the gastrointestinal lumen is independent of posture, pH, and gastrointestinal motility in fed or fasting conditions. The biologically inert components of the tablet remain intact during gastrointestinal transit and are eliminated in the feces as an insoluble shell.

The formulations disclosed in U.S. Pat. Nos. 5,160,744; 5,190,765; and 5,252,338 and thus the currently marketed Covera-HS™ tablet formulation, has several limitations. The semi-permeable membrane that surrounds the drug and push compositions is permeable to the passage of the external fluid but is substantially impermeable to the passage of the drug. Delivery of the drug is purported to be essentially constant. However, the release rate of the drug from the dosage form is constant only until the concentration of the drug inside the dosage form falls below saturation. Thereafter, the osmotic gradient decreases across the membrane and the release rate of the drug from the dosage form gradually declines to zero. As a result, the formulations disclosed in U.S. Pat. Nos. 5,160,744; 5,190,765; and 5,252,338 and thus the currently marketed Covera-HS™ tablet formulation does not reliably release verapamil at a sustained rate. As well, upon ingestion, the semi-permeable membrane maintains its physical and chemical integrity during gastrointestinal transit and is eliminated in the feces as an insoluble shell. The osmotically active agents may lack the ability to imbibe sufficient fluid for the maximum self-expansion needed for urging all of the drug from the dosage form. Therefore, due to the nature of the osmotic drug delivery system, some of the drug remains in the insoluble, inflexible shell and is thus not available for the desired absorption and effect. In addition, the formulations may be manufactured with solvents (used to dissolve cellulose ester polymers in the semi-permeable membrane) that are not environmentally friendly, expensive and also require expensive manufacturing processes that need explosion proof equipment and laser guns to drill holes on the surface of the dosage forms. Furthermore, these processes may be unhealthy and may even be harmful to the employees involved in manufacturing these products. The residual solvents remaining in these products may also cause adverse side effects among users of these products.

It is accordingly one object of the present invention to provide a novel and improved pharmaceutical composition for delivering an active ingredient or a plurality of active ingredients from the pharmaceutical composition at a sustained rate after a desired time delay or a controlled onset of release while avoiding the disadvantages of the prior art compositions.

It is a further object of the present invention is to provide pharmaceutical compositions that begin to release active ingredients from the pharmaceutical compositions at a predetermined time delay or controlled onset after administration of the pharmaceutical compositions and which continue releasing the same active ingredients from the pharmaceutical compositions at a predetermined release rate such that the blood levels achieved by such pharmaceutical compositions provide a significant therapeutic benefit to patients suffering from various disease states.

It is yet another object of the present invention to provide a method for administering active ingredients to a patient in need of therapy by administering a pharmaceutical composition which provides a time delay of between about 30 minutes to 6 hours in the delivery of the active ingredient.

It is yet another object of the present invention to provide a method for producing a delayed therapeutic effect of between about 30 minutes to 6 hours in a patient in need of therapy.

It is yet another object of the present invention to provide a method of preparing a pharmaceutical composition for controlled onset and sustained release of an active ingredient.

It is yet another object of the present invention to provide a pharmaceutical composition that delivers an active ingredient selected from the group consisting of very soluble active ingredients, freely soluble active ingredients, soluble active ingredients, sparingly soluble active ingredients, slightly soluble active ingredients, very slightly soluble active ingredients and practically insoluble, or insoluble active ingredients in a controlled and sustained rate to a patient in need of therapy with a controlled onset of between about 30 minutes and 6 hours.

It is yet another object of the present invention to provide a pharmaceutical composition that delivers glipizide (insoluble drug) in a controlled and sustained rate to a patient in need of glipizide therapy with a controlled onset of about 2 hours.

It is yet another object of the present invention to provide a pharmaceutical composition that delivers verapamil HCl (soluble drug) in a controlled and sustained release rate to a patient in need of verapamil therapy with a controlled onset of about 2 hours.

Further and other objects of the invention will become apparent to those skilled in the art from reading the following summary of the invention and the preferred embodiments described and illustrated herein.

SUMMARY OF THE INVENTION

In accordance with an aspect of the present invention, there is provided a pharmaceutical composition for controlled onset and sustained release of an active ingredient, said composition comprising:
(i) a core comprising:
 (a) an active ingredient;
 (b) a hydrophilic carrier;
 (c) a hydrodynamic diffusion enhancer; and optionally
 (d) conventional pharmaceutically acceptable excipients selected from the group consisting of binders, fillers and lubricants and combinations thereof; and
(ii) a functional coating membrane surrounding said core.

In accordance with a further aspect of the present invention, there is provided a pharmaceutical composition for controlled onset and sustained release of an active ingredient, said composition comprising:
(i) a core comprising:
 (a) an active ingredient;
 (b) a hydrophilic carrier;
 (c) a hydrodynamic diffusion enhancer; and optionally
 (d) conventional pharmaceutically acceptable excipients selected from the group consisting of binders, fillers and lubricants and combinations thereof;
(ii) a functional coating membrane surrounding said core; and
(iii) a top coating membrane surrounding said functional coating membrane.

In accordance with a further aspect of the present invention, there is provided a pharmaceutical composition for controlled onset and sustained release of an active ingredient, said composition comprising:
(i) a core comprising:
 (a) an active ingredient;
 (b) a hydrophilic carrier;
 (c) a hydrodynamic diffusion enhancer; and optionally
 (d) conventional pharmaceutically acceptable excipients selected from the group consisting of binders, fillers and lubricants and combinations thereof;
(ii) a seal coating membrane surrounding said core; and
(iii) a functional coating membrane surrounding said seal coating membrane.

In accordance with a further aspect of the present invention, there is provided a pharmaceutical composition for controlled onset and sustained release of an active ingredient, said composition comprising:
(i) a core comprising:
 (a) an active ingredient;
 (b) a hydrophilic carrier;
 (c) a hydrodynamic diffusion enhancer; and optionally
 (d) conventional pharmaceutically acceptable excipients selected from the group consisting of binders, fillers and lubricants and combinations thereof;

(ii) a seal coating membrane surrounding said core;
(iii) a functional coating membrane surrounding said seal coating membrane, and
(iv) a top coating membrane surrounding said functional coating membrane.

In an embodiment of the present invention, the active ingredient in the core is dispersed as a solid in a matrix comprising the hydrophilic carrier, the hydrodynamic diffusion enhancer, and the optional conventional pharmaceutically acceptable excipients selected from the group consisting of binders, fillers and lubricants and combinations thereof.

In an embodiment of the present invention, the core is in a form selected from the group consisting of a tablet, a caplet, a sphere, a spheroid, a granule, a pellet or the like, which form allows for coating.

In an embodiment of the present invention, the pharmaceutical composition is a finished dosage form selected from the group consisting of a tablet, a caplet, a capsule, a sphere, a spheroid, a pellet, a troche, a cachet, a pill or the like in all sizes, shapes and colours.

In an embodiment of the present invention, the core is developed such that the release rate of the active ingredient from the uncoated core is faster than the release rate of the active ingredient from the finished dosage form (coated core). The ratio of hydrophilic carrier to hydrodynamic diffusion enhancer and to the optional conventional pharmaceutically acceptable excipients is optimized to obtain the desired release rate of the active ingredient from the core.

In an embodiment of the present invention, the active ingredient is any ingredient that provides a significant therapeutic benefit to humans or animals when released from the pharmaceutical compositions in a controlled onset and sustained release profile.

Preferably, the active ingredients which are suitable for use in the pharmaceutical compositions of the present invention are selected from the group consisting of very soluble drugs, freely soluble drugs, soluble drugs, sparingly soluble drugs, slightly soluble drugs, very slightly soluble drugs and practically insoluble, or insoluble drugs. According to *Remington: The Science and Practice of Pharmacy*, $19^{th}$ Edition, ed. Alfonso R. Gennaro, Vol. 1, Table 1, p. 195, Mack Publishing Company, Easton, Pa. 18042, the above-mentioned descriptive terms for solubility are defined. Specifically, very soluble means that less than 1 part of solvent is required to dissolve 1 part of solute. Freely soluble means that from 1 to 10 parts of solvent are required to dissolve 1 part of solute. Soluble means that from 10 to 30 parts of solvent are required to dissolve 1 part of solute. Sparingly soluble means that from 30 to 100 parts of solvent are required to dissolve one part of solute. Slightly soluble means that from 100 to 1000 parts of solvent are required to dissolve one part of solute. Very slightly soluble means that from 1000 to 10,000 parts of solvent are required to dissolve 1 part of solute. Practically insoluble, or insoluble means that more than 10,000 parts of solvent are required to dissolve 1 part of solute.

Preferably, the active ingredients which are suitable for use in the pharmaceutical compositions of the present invention are selected from the group consisting of anti-inflammatory drugs such as phenylbutazone, indomethacin, naproxen, ibuprofen, flurbiprofen, diclofenac, dexamethasone, oxaprozin, prednisone and prednisolone; coronary dilator drugs such as glyceryl trinitrate, isosorbide dinitrate and pentaerythritol tetranitrate; peripheral vasodilator drugs such as naftidrofuryl oxalate, cyclandelate and nicotinic acid; anti-infective drugs such as erythromycin, cephalexin, naldixic acid, clarithromycin, cefuroxime, cefaclor, cefprozil, zidovudine, acyclovir, ofloxacin, ciprofloxacillin, azithromycin and flucloxacillin sodium; psychotropic and/or an antianxiety drugs such as fluazepam, diazepam, amitryptaline, doxepine, thioridazine, trifluperazine, fluphenazine, piperothiazine, haloperidol, maprotiline hydrochloride, imipremine, clorazepate, estazolam, lorazepam, alprazolam, bupropion, fluoxetine, buspirone, clonazepam, sertaline, zolpidem, desmethylimipramine, lithium carbonate, lithium sulfate and methylphenidate; central stimulant drugs such as isoproterinol, amphetamine sulphate and amphetamine hydrochloride; antihistamine drugs such as chlorpheniramine, brompheniramine, fexofenadine, loratidine and diphenhydramine; laxative and/or antidiarrheal drugs such as bisacodyl, magnesium hydroxide, loperamide, diphenoxylate, and dioctyl sodium sulfosuccinate; decongestant drugs such as phenylpropanolamine and pseudoephedrine; vitamin substances such as alphatocopherol, thiamin, pyridoxine and ascorbic acid; antacids such as aluminum trisilicate, aluminum hydroxide, cimetidine, ranitidine, famotidine, omeprazole and nizatidine; gastrointestinal sedatives such as propantheline bromide and metoclorpramide; cerebral vasodilators such as soloctidilum, naftidrofuryl oxalate, co-dergocrine mesylate, papaverine and pentoxifylline; anti-anginal drugs such as isosorbide dinitrate, pentaerythritol tetranitrate, verapamil, nifedipine, diltiazem, and glyceryl trinitrate; antiarrythmics such as verapamil, nifedipine, diltiazem, disopyramide, bretylium tosylate, quinidine sulfate, quinidine gluconate and procainamide; antihypertensives such as methyldopa, captopril, hydralazine, propranolol, labetalol, sotalol, terazosin, enalapril, lisinopril, quinalapril, benazepril, ramipril, clonidine, fosinopril, felodipine, immodipine and amlodipine; vasoconstrictors such as ergotamine; substances which influences blood coagulability such as protamine sulfate and epsilon aminocaproic acid; hypnotics such as dichloral phenazone, nitrazepam and temazepam; antinauseants such as chlorpromazine and promethazine theoclate; anticonvulsants such as sodium valproate, phenytoin sodium, divalproex sodium and carbamezipine; neuromuscular drugs such as dentrolene sodium; hypoglycemic agents such as diabenese, insulin, glyburide, glipizide and troglitazone; drugs used in treating thyroid gland disorders such as thyroxin, triiodothyronine and propylthiouracil; diuretics such as furosemide, chlorthalidone, hydrochlorthiazide, spironolactone, triampterene and indapamide; uterine relaxant medications such as ritodrine; appetite suppressants such as asphenteramine, diethylproprion hydrochloride and fenfluramine hydrochloride; erythropoietic substances such as folic acid, calcium gluconate and ferrous sulphate; antiasthmatic drugs such as aminophylline, theophylline, orciprenaline sulphate, terbutaline sulphate, albuterol and salbutamol; expectorants such as carbocisteine and guaiphenesin; cough suppressants such as noscapine, codeine phosphate, codeine sulfate, oxycodone, dihydrocodeine tartrate, oxycodeinone and dextromethorphan; antiuricemic drugs such as allopurinol, probenecid and sulphinpyrazone; antiseptics such as cetylpyridinium chloride, tyrothricin and chlorhexidine; antilipidimic or anticholesterol agents such as lovastatin, gemfibrozil, simvastatin and pravastatin; pharmaceutically acceptable salts thereof and combinations thereof. Any active ingredient from a very soluble drug to a practically insoluble or insoluble drug would be a suitable active ingredient for the present invention and the active ingredients discussed above are used as examples only.

In an embodiment of the present invention, the hydrophilic carrier is one or more hydrophilic polymeric excipients in any desired ratio to provide a desired release profile of the active ingredient from the pharmaceutical composition.

Preferably, the hydrophilic carrier is a homopolysaccharide or a heteropolysaccharide, preferably selected from the group consisting of xanthan gum, locust bean gum, propylene glycol ester, galactomannan, glucomannan, guar gum, gum acacia, gum tragacanth, alkali metal carageenates, alginates, cellulose alkyl carboxylates, carboxymethyl cellulose, carboxyethyl cellulose, alkali metal salts of cellulose alkyl carboxylates, sodium carboxymethyl cellulose, carboxypolymethylene, hydroxypropyl methylcelluloses, hydroxypropyl cellulose, hydroxyethyl cellulose, hydroxyethyl methyl cellulose, polyethylene glycols and polyethylene oxides, gellan gum, alginate salts, natural polysaccharides, gum arabica, etc. and combinations thereof. Some examples of polyethylene glycols and polyethylene oxides commercially available are those under the tradename Polyox® (Union Carbide, Danbury, Conn.). Any polymeric material that can hydrate and gel in the presence of water would be a suitable hydrophilic carrier for the pharmaceutical compositions of the present invention.

Preferably, the hydrophilic carrier is hydroxypropyl methylcellulose, preferably having a viscosity between about 5 cps and 100,000 cps, a hydroxypropoxyl content between about 7 and 12%, a methoxyl content between about 19 and 30%.

The molecular weight of the hydrophilic carrier is selected based on the solubility of the active ingredient. Low molecular weight grade hydrophilic carriers are utilized for insoluble drug substances. High molecular weight grade hydrophilic carriers are utilized for soluble drug substances. Preferably, a blend of low and high molecular weight hydrophilic carriers are selected such that any desired molecular weight can be accomplished by adjusting the ratio of the blend.

In another embodiment of the present invention, the hydrophilic carrier is a blend of hydroxypropyl methylcelluloses having different molecular weights and/or viscosities.

Preferably, the ratio of the blend of hydroxypropyl methylcelluloses can vary from 1:99 to 99:1 with respect to low and higher molecular weight of hydroxypropyl methylcelluloses.

Preferably, the hydrophilic carrier in said core is present in a concentration of about 5 to 99% W/W of the weight of the core.

In an embodiment of the present invention, the hydrodynamic diffusion enhancer is a substance which has the inherent capability of drawing water towards it, thereby increasing the rate at which water diffuses through a membrane, then absorbs this water, and swells and increases its volume and creates an internal hydrodynamic pressure.

Preferably, the hydrodynamic diffusion enhancer is selected from the group consisting of gellan gum, starches, clays, celluloses, cellulose derivatives, alginates, crospovidone (Polyplasdone® and Polyplasdone® XL (ISP, Wayne, N.J.)), croscarmellose sodium (Ac-Di-Sol®, FMC Corp., Philadelphia, Pa.), sodium starch glycolate (Explotab®, Penwest, Patterson, N.Y.) and combinations thereof. Any excipient which has the inherent capability of drawing water towards it, thereby increasing the rate at which water diffuses through a membrane, then absorbs this water, and swells and increases its volume and creates an internal hydrodynamic pressure would be capable of functioning as a hydrodynamic diffusion enhancer and thus would be a suitable hydrodynamic diffusion enhancer for the pharmaceutical compositions of the present invention.

Preferably, the hydrodynamic diffusion enhancer in said core is present in a concentration of about 5 to 60% W/W of the weight of the core.

In an embodiment of the present invention, the binders are substances which can be used to granulate powders that may not otherwise have adequate flowability characteristics required for the tabletting process.

Preferably, the fillers and binders are each selected from the group consisting of polyethylene glycols, microcrystalline cellulose, lactose, starches, starch derivatives, mannitol, sorbitol, dextrose, sucrose, maltodextrin, celluloses, cellulose derivatives, hydroxypropyl methylcellulose, hydroxypropyl ethylcellulose, polyvinyl pyrrolidone, ethyl cellulose, hydroxypropyl cellulose, hydroxyethyl cellulose or other sugars, polysaccharides and gums, etc. and combinations thereof. Any conventional binder would also be suitable as a binder in the pharmaceutical compositions of the present invention.

Preferably, the fillers in said core are present in a concentration of about 2 to 40% W/W of the weight of the core.

Preferably, the binders in said core are present in a concentration of bout 1 to 10% W/W of the weight of the core.

In an embodiment of the present invention, the lubricants and flow promoters are selected from the group consisting of stearic acid, talc, waxes, stearic acid salts, stearic acid derivatives, sodium stearyl fumarate, corn starch, silica derivatives and combinations thereof.

Preferably, the lubricants in said core are present in a concentration of about 0.25 to 4% W/W of the weight of the core.

In an embodiment of the present invention, the optional seal coating membrane, which is also typically known as a film coat, functions to seal all surface pores and to provide a uniform surface for the next coating step.

Preferably, the optional seal coating membrane is present in a concentration of about 0–5% W/W of the core.

The optional seal coating membrane is obtained by preferably spray coating seal coating dispersions onto the surface of uncoated cores using appropriate coating equipment. Usually these dispersions contain low viscosity hydrophilic polymers such as hydroxypropyl methylcellulose and hydroxypropyl cellulose, and plasticizers such as polyethylene glycol 400. These dispersions are commercially available as Opadry® Clear and Opadry® both from Colorcon, West Point, Pa. Similar seal coating dispersions are also available from other suppliers. The seal coating membrane is applied to the surface of an uncoated core to smooth out the surface of the core.

In an embodiment of the present invention, the functional coating membrane is applied on top of the core or on top of the optional seal coating membrane.

Preferably, the functional coating membrane is an aqueous polymeric dispersion comprising dispersed plasticizers, film extenders and diffusion enhancers.

Preferably, the functional coating membrane comprises ethylcellulose as an aqueous dispersion, preferably with appropriate coating ingredients dispersed therein.

Preferably, the ratio of the polymer to film extender in the aqueous polymeric dispersion of the functional coating membrane is from about 0.25–0.75 to 0.99–0.01.

Functional coating membranes are obtained by preferably spraying functional coating dispersions onto the surface of the seal coated cores. However, these functional coating dispersions can also be coated straight onto the surface of the uncoated cores. These functional coating dispersions preferably contain a hydrophobic polymer such as ethyl cellulose, a plasticizer, a film extender/diffusion enhancer, and other excipients such as detackifiers or opacifiers, etc. The hydrophobic polymer is mixed with a film extender/diffusion enhancer to give the hydrophobic polymer some degree of hydrophilicity. The plasticizer is added to reduce the glass transition temperature ($T_g$) of the polymer so that it can be coalesced at a lower temperature (such as 60° C.). The plasticizer also makes the functional coating membrane flexible so that it can stretch to some degree without breaking. Examples of such commercially available aqueous polymeric dispersions suitable for use in the present invention are Surelease® (Colorcon, West Point, Pa.) and Aquacoat® (FMC Corp, Philadelphia, Pa.). The plasticizers and film extender/diffusion enhancers are dispersed into the commercially available functional coating dispersions such as Aquacoat® or Surelease® and then sprayed onto the surface of the uncoated or seal coated cores. Other functional coating dispersions preferably contain acrylic methacrylic copolymers. Examples of such functional coating dispersions commercially available are Eudragit® (Rohm Pharma GmbH, Weiterstadt, Germany). Aqueous polymeric dispersions containing acrylic methacrylic copolymers, cellulose acetate and other cellulose derivative polymers can be formulated in to aqueous polymers and used for the same purpose. Similar functional coating dispersions can be prepared with other hydrophilic or lyophilize polymers which would be suitable for this purpose.

Preferably, the functional coating membrane is present in a concentration of about 1–25% W/W of the weight of the core.

In an embodiment of the present invention, the optional top coating membrane allows the functional coating membrane to be coalesced.

Preferably, the optional top coating membrane is an aqueous coating dispersion, and preferably the aqueous coating dispersion is present in a concentration of about 0–5% W/W of the core.

Preferably, the aqueous coating dispersion of the optional top coating membrane further comprises dispersed colours.

The aqueous dispersion of the optional top coating membrane may contain any desirable color to color the tablets.

The optional top coating membrane is obtained by preferably spraying top coating dispersions onto the surface of the functional coating membrane. These top coating dispersions are commercially available as Opadry® white or Opadry® red, etc., named after the colorant present in the dispersion. Other equivalent brands of functional coating dispersions commercially available in the market are also suitable.

In accordance with a further aspect of the present invention, there is provided a method for administering an active ingredient to a patient in need of therapy, which method comprises:

administering a pharmaceutical composition to the patient, said composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof; and
  (ii) a functional coating membrane surrounding said core.

In accordance with a further aspect of the present invention, there is provided a method for administering an active ingredient to a patient in need of therapy, which method comprises:

administering a pharmaceutical composition to the patient, said composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof;
  (ii) a functional coating membrane surrounding said core; and
  (iii) a top coating membrane surrounding said functional coating membrane.

In accordance with a further aspect of the present invention, there is provided a method for administering an active ingredient to a patient in need of therapy, which method comprises:

administering a pharmaceutical composition to the patient, said composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof;
  (ii) a seal coating membrane surrounding said core; and
  (iii) a functional coating membrane surrounding said seal coating membrane.

In accordance with a further aspect of the present invention, there is provided a method for administering an active ingredient to a patient in need of therapy, which method comprises:

administering a pharmaceutical composition to the patient, said composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof;
  (ii) a seal coating membrane surrounding said core;
  (iii) a functional coating membrane surrounding said seal coating membrane, and
  (iv) a top coating membrane surrounding said functional coating membrane.

In accordance with a further aspect of the present invention, there is provided a method for producing a delayed therapeutic effect of 30 minutes to 6 hours in a patient in need of therapy, wherein the method comprises:
(A) administering to the patient a pharmaceutical composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof; and
  (ii) a functional coating membrane surrounding said core;
(B) imbibing and/or diffusing fluid into the pharmaceutical composition to provide a delayed delivery of the active ingredient of 30 minutes to 6 hours by the functional coating membrane; and (C) administering the active ingredient at a delayed time to the patient in need of therapy.

In accordance with a further aspect of the present invention, there is provided a method for producing a delayed therapeutic effect of 30 minutes to 6 hours in a patient in need of therapy, wherein the method comprises:

(A) administering to the patient a pharmaceutical composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof;
  (ii) a functional coating membrane surrounding said core; and
  (iii) a top coating membrane surrounding said functional coating membrane;
(B) imbibing and/or diffusing fluid into the pharmaceutical composition to provide a delayed delivery of the active ingredient of 30 minutes to 6 hours by the functional coating membrane; and
(C) administering the active ingredient at a delayed time to the patient in need of therapy.

In accordance with a further aspect of the present invention, there is provided a method for producing a delayed therapeutic effect of 30 minutes to 6 hours in a patient in need of therapy, wherein the method comprises:

(A) administering to the patient a pharmaceutical composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof;
  (ii) a seal coating membrane surrounding said core; and
  (iii) a functional coating membrane surrounding said seal coating membrane;
(B) imbibing and/or diffusing fluid into the pharmaceutical composition to provide a delayed delivery of the active ingredient of 30 minutes to 6 hours by the functional coating membrane; and
(C) administering the active ingredient at a delayed time to the patient in need of therapy.

In accordance with a further aspect of the present invention, there is provided a method for producing a delayed therapeutic effect of 30 minutes to 6 hours in a patient in need of therapy, wherein the method comprises:

(A) administering to the patient a pharmaceutical composition comprising:
  (i) a core comprising:
    (a) an active ingredient;
    (b) a hydrophilic carrier;
    (c) a hydrodynamic diffusion enhancer; and optionally
    (d) conventional pharmaceutically acceptable excipients selected from the group consisting of binders, fillers and lubricants and combinations thereof;
  (ii) a seal coating membrane surrounding said core;
  (iii) a functional coating membrane surrounding said seal coating membrane, and
  (iv) a top coating membrane surrounding said functional coating membrane;
(B) imbibing and/or diffusing fluid into the pharmaceutical composition to provide a delayed delivery of the active ingredient of 30 minutes to 6 hours by the functional coating membrane; and
(C) administering the active ingredient at a delayed time to the patient in need of therapy.

In accordance with a further aspect of the present invention, there is provided a method for preparing a controlled onset sustained release pharmaceutical composition, said composition comprising:
  (i) a core comprising:
    (a) an active ingredient;
    (b) a hydrophilic carrier;
    (c) a hydrodynamic diffusion enhancer; and
    (d) optionally conventional pharmaceutically acceptable excipients selected from the group consisting of binders, fillers and lubricants; and
  (ii) a functional coating membrane surrounding said core wherein the method comprises:
  (iii) blending the active ingredient with the hydrophilic carrier, the hydrodynamic diffusion enhancer and optionally with the conventional pharmaceutically acceptable excipients;
  (iv) granulating the blend with a binder to obtain a wet mass;
  (v) drying the wet mass at 60° C. for 3 hours;
  (vi) lubricating the granules with a lubricant;
  (vii) compressing the lubricated granules to form a core;
  (viii) applying a functional coating membrane containing aqueous polymeric dispersions, with dispersed plasticizers, and film extenders/diffusion enhancers to the surface of the core;
  (ix) curing of the coated core at a temperature range of 30° C.–80° C. for up to 12 hours.

In accordance with a further aspect of the present invention, there is provided a method for preparing a controlled onset sustained release pharmaceutical composition, said composition comprising:
  (i) a core comprising:
    (a) an active ingredient;
    (b) a hydrophilic carrier;
    (c) a hydrodynamic diffusion enhancer; and
    (d) optionally conventional pharmaceutically acceptable excipients selected from the group consisting of binders, fillers and lubricants;
  (ii) a functional coating membrane surrounding said seal coating membrane; and
  (iii) a top coating membrane surrounding said functional coating membrane, wherein the method comprises:
  (iv) blending the active ingredient with the hydrophilic carrier, the hydrodynamic diffusion enhancer and optionally with the conventional pharmaceutically acceptable excipients;
  (v) granulating the blend with a binder to obtain a wet mass;
  (vi) drying the wet mass at 60° C. for 3 hours;
  (vii) lubricating the granules with a lubricant;
  (viii) compressing the lubricated granules to form a core;
  (ix) applying a functional coating membrane containing aqueous polymeric dispersions, with dispersed plasticizers, and film extenders/diffusion enhancers to the surface of the core;
  (x) applying a top coating membrane with aqueous coating dispersions to the surface of the functional coating membrane; and (xi) curing of the coated core at a temperature range of 30° C.–80° C. for up to 12 hours.

In accordance with a further aspect of the present invention, there is provided a method for preparing a controlled onset sustained release pharmaceutical composition, said composition comprising:
(i) a core comprising:
  (a) an active ingredient;
  (b) a hydrophilic carrier;
  (c) a hydrodynamic diffusion enhancer; and
  (d) optionally conventional pharmaceutically acceptable excipients selected from the group consisting of binders, fillers and lubricants;
(ii) a seal coating membrane surrounding said core;
(iii) a functional coating membrane surrounding said seal coating membrane; wherein the method comprises:
(iv) blending the active ingredient with the hydrophilic carrier, the hydrodynamic diffusion enhancer and optionally with the conventional pharmaceutically acceptable excipients;
(v) granulating the blend with a binder to obtain a wet mass;
(vi) drying the wet mass at 60° C. for 3 hours;
(vii) lubricating the granules with a lubricant;
(viii) compressing the lubricated granules to form a core;
(ix) applying a seal coating membrane to the surface of the core to smooth out the surface;
(x) applying a functional coating membrane containing aqueous polymeric dispersions, with dispersed plasticizers, and film extenders/diffusion enhancers to the surface of the seal coating membrane;
(xi) curing of the coated core at a temperature range of 30° C.–80° C. for up to 12 hours.

In accordance with a further aspect of the present invention, there is provided a method for preparing a controlled onset sustained release pharmaceutical composition, said composition comprising:
(i) a core comprising:
  (a) an active ingredient;
  (b) a hydrophilic carrier;
  (c) a hydrodynamic diffusion enhancer; and
  (d) optionally conventional pharmaceutically acceptable excipients selected from the group consisting of binders, fillers and lubricants;
(ii) a seal coating membrane surrounding said core;
(iii) a functional coating membrane surrounding said seal coating membrane; and
(iv) a top coating membrane surrounding said functional coating membrane, wherein the method comprises:
(v) blending the active ingredient with the hydrophilic carrier, the hydrodynamic diffusion enhancer and optionally with the conventional pharmaceutically acceptable excipients;
(vi) granulating the blend with a binder to obtain a wet mass;
(vii) drying the wet mass at 60° C. for 3 hours;
(viii) lubricating the granules with a lubricant;
(ix) compressing the lubricated granules to form a core;
(x) applying a seal coating membrane to the surface of the core to smooth out the surface;
(xi) applying a functional coating membrane containing aqueous polymeric dispersions, with dispersed plasticizers, and film extenders/diffusion enhancers to the surface of the seal coating membrane;
(xii) applying a top coating membrane with aqueous coating dispersions to the surface of the functional coating membrane; and
(xiii) curing of the coated core at a temperature range of 30° C.–80° C. for up to 12 hours.

In accordance with a further aspect of the present invention, there is provided a method for controlling the duration of the time delay before which the active ingredient is released from the pharmaceutical composition and the duration of release of the active ingredient(s) after such time delay.

The present invention provides pharmaceutical compositions that contain many ingredients which perform many functions. It is the combination of some or all of these ingredients in the pharmaceutical compositions of the present invention that release the desired active ingredient from the pharmaceutical composition with the desired release profile.

The mechanism of release of the controlled onset sustained release pharmaceutical compositions of the present invention described above is as follows:

1) As the dosage form comes into contact with the gastrointestinal fluids, the optional top coating membrane, when present, hydrates and erodes, thus exposing the functional coating membrane to the environment of the gastrointestinal tract. With time, the gastrointestinal fluids hydrate the film extender/diffusion enhancer in the functional coating membrane and create channels which penetrate the functional coating membrane of the dosage form, thus exposing the optional seal coating membrane to the gastrointestinal fluids. The amount of functional coating membrane applied to the core and the ratio of the polymer to film extender/diffusion enhancer in the functional coating membrane may be adjusted to control the rate at which the gastrointestinal fluids penetrate the functional coating membrane. The optional seal coating membrane, when present, hydrates and erodes, thus exposing the core to the gastrointestinal fluids.

2) The hydrodynamic diffusion enhancer in the core promotes the entry of the gastrointestinal fluids into the core by working as a sponge inside the core. When the required amount of gastrointestinal fluid enters the core, the hydrodynamic diffusion enhancer hydrates and begins to swell. The hydrophilic carrier also hydrates and swells during this time and contributes to the hydrodynamic swelling force provided by the hydrodynamic diffusion enhancer. The ratio of the amount of hydrophilic carrier to hydrodynamic diffusion enhancer can be adjusted to control the extent and degree of swelling by the core. The active ingredient also comes into contact with the gastrointestinal fluids and starts to dissolve. While the hydrodynamic diffusion enhancer and the hydrophilic carrier are swelling inside the core, the functional coating membrane surrounding the core prevents release of the active ingredient, resulting in a time delay in the onset of release of the active ingredient from the dosage form. The predetermined time delay can be varied from between about 30 minutes to 6 hours.

3) Upon further swelling, the core stretches and expands the functional coating membrane surrounding the core and helps the active ingredient to permeate through the functional coating membrane and pass out of the dosage form. The rate at which the active ingredient can diffuse out of the dosage form is controlled by the composition of the core and the composition and amount of the functional coating membrane applied to the core. The amount of hydrodynamic diffusion enhancer in the core may be adjusted such that the hydrodynamic swelling force generated by this material and the time required to generate this force are adequate to stretch and expand the functional coating membrane by the end of the required time delay in order to facilitate the release of the active ingredient from the dosage form.

4) Depending upon the composition of the core and the amount of the functional coating membrane applied to the core, the swelling core may generate adequate hydrodynamic swelling force to eventually rupture the functional coating membrane. If and when the functional coating membrane ruptures, it ruptures around the edges of the dosage form. Rupturing in this way may leave the functional coating membrane on the upper and the bottom surfaces of the dosage form intact for an extended period of time. The remaining intact functional coating membrane together with the fully hydrated core control the release of the active ingredient from the dosage form in a substantially zero order fashion for the desired period of time. The release of the active ingredient from the dosage form after the programmed time delay can be varied from a substantially zero order rate of release to a substantially first order rate of release. The sustained release of the active ingredient from the dosage form can be adjusted from between about 6 to 24 hours post the initial programmed time delay.

The pharmaceutical compositions of the present invention have several advantages. The present invention enables persons skilled in the art to manufacture controlled onset and sustained release pharmaceutical compositions using mostly aqueous dispersions and using conventional equipment which are used by most pharmaceutical companies. Thus, the pharmaceutical compositions disclosed in the present invention are essential to deliver active ingredients to humans or animals in an environmentally friendly form, with all of the desired functionality of controlled onset and sustained release, with no risk of adverse side effects from residual solvents.

The controlled onset feature of the present pharmaceutical compositions provide for: a) release of the active ingredient at specific locations along the gastrointestinal tract, or b) colonic release of the active ingredient or c) protection of the stomach from any damage the active ingredient may cause or d) facilitation of high levels of the active ingredient in the blood during any desired time period during the day or night such as, early morning hours to provide maximum protection against heart attacks, or e) the treatment of diseases that occur only in certain portions of the gastrointestinal tract such as ulcerative colitis in the colon, etc.

The sustained release feature of the present pharmaceutical compositions are extremely useful in providing uniform blood levels of active ingredients to obtain a more consistent pharmacological response, reduce peak to trough ratios and thereby reduce the incidence and/or severity of side effects, improve patient compliance, reduce the cost of overall treatment, etc.

Thus, combining both the features of controlled onset and sustained release into a single pharmaceutical composition along with using environmentally friendly manufacturing processes that do not use ozone depleting solvents and/or carcinogenic solvents to produce such a pharmaceutical composition and using conventional manufacturing equipment, the pharmaceutical compositions of the present invention are a significant advancement over the current state of art technology (prior art).

BRIEF DESCRIPTION OF THE DRAWINGS

The present invention will be further understood from the following detailed description with references to the following drawings is which.

Similar references are used in different figures to denote similar components.

DETAILED DESCRIPTION OF THE PREFERRED EMBODIMENTS

Figure 1:
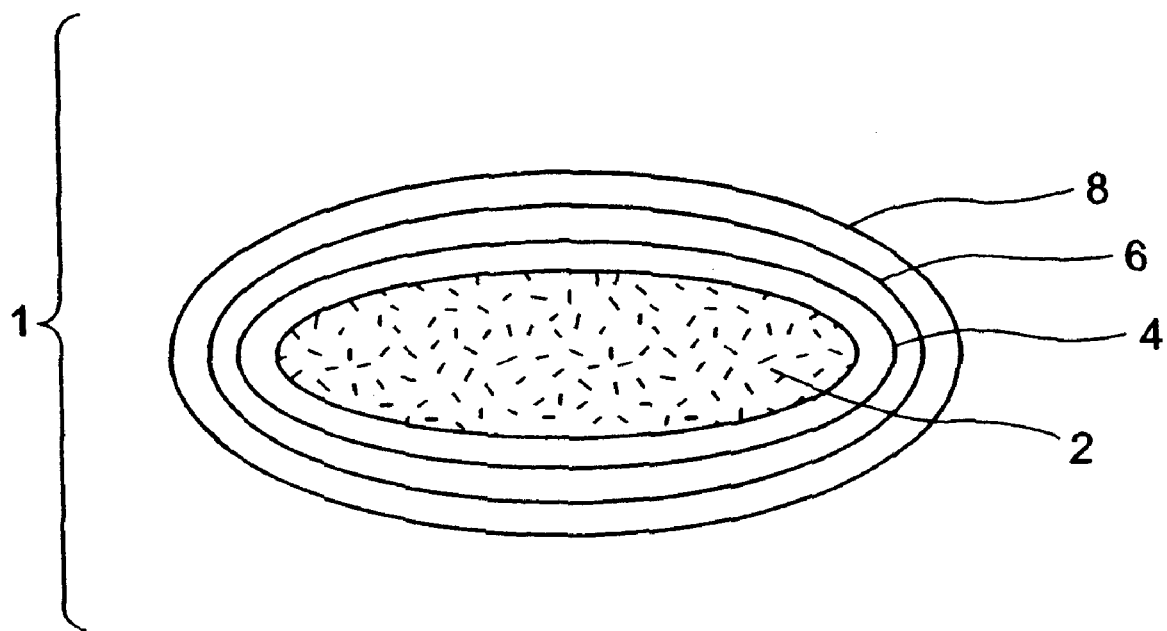
FIG. 1 is a view of the horizontal cross section of a pharmaceutical composition according to one embodiment of the present invention.
Figure 2:
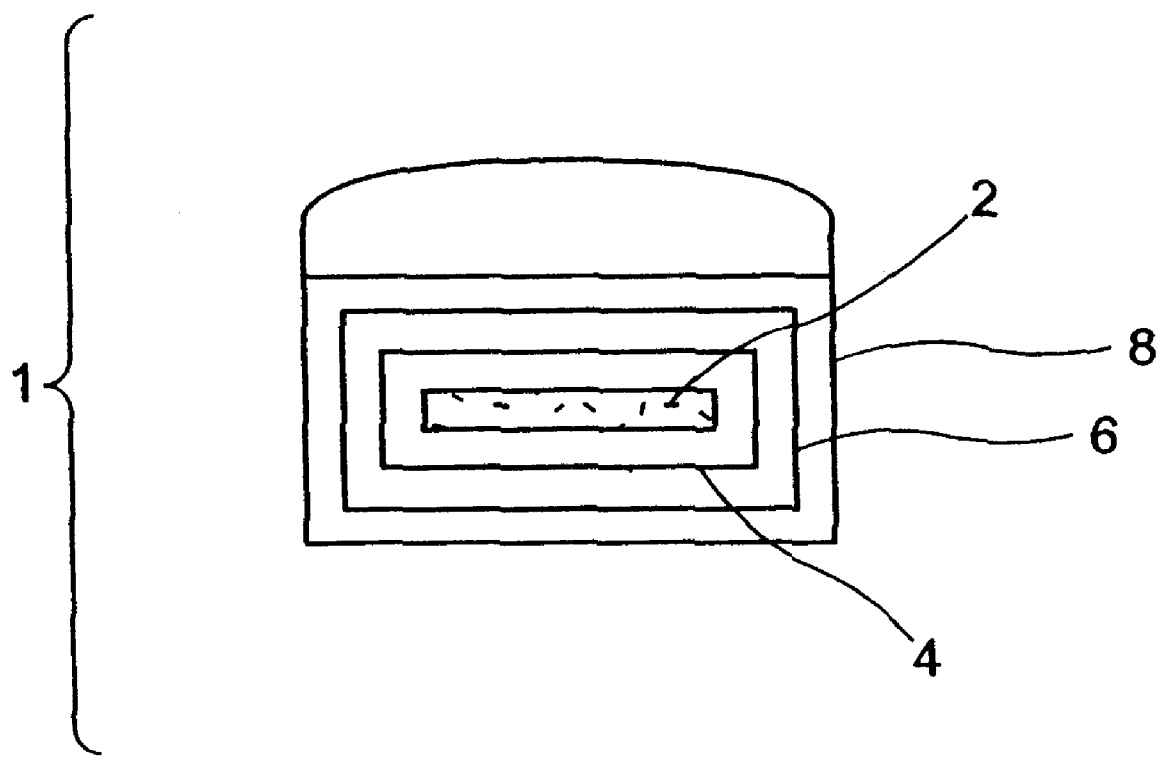
FIG. 2 is a perspective view of a vertical cross section of a pharmaceutical composition according to one embodiment of the present invention.

Referring now to FIGS. 1 and 2 for a preferred embodiment of the present invention, there is provided a pharmaceutical composition 1 comprising a core 2, a seal coating membrane 4 surrounding the core 2, a functional coating membrane 6 surrounding the seal coating membrane 4 and a top coating membrane 8 surrounding the functional coating membrane 6.

Figure 3:
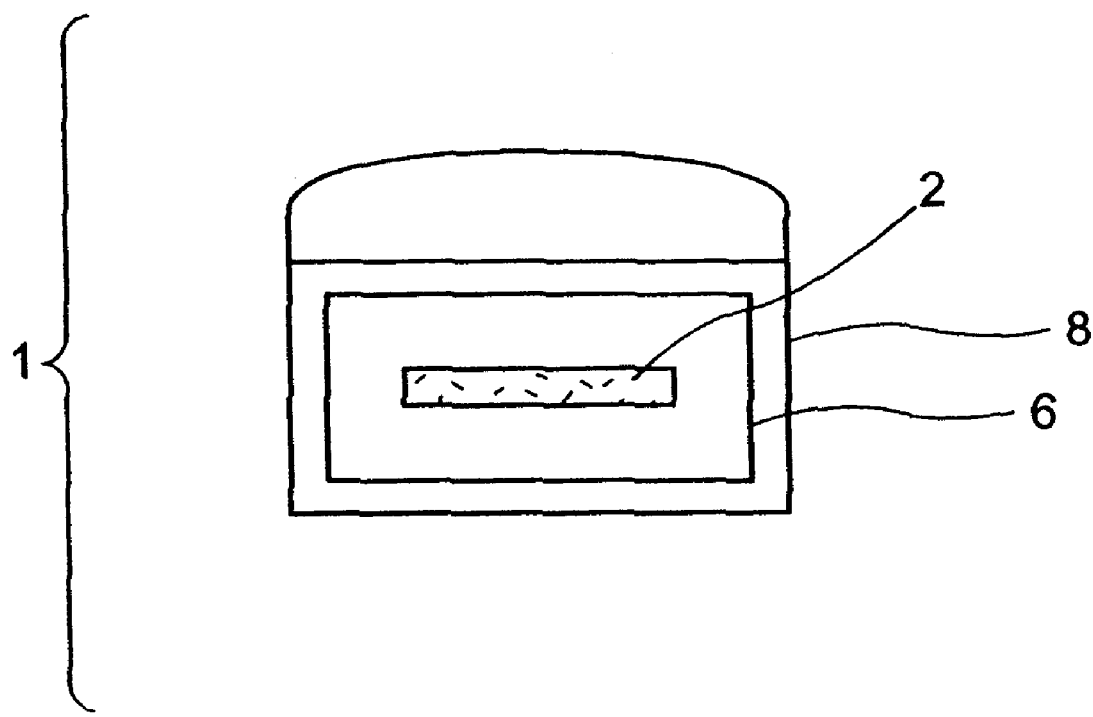
FIG. 3 is a perspective view of a vertical cross section of a pharmaceutical composition according to another embodiment of the present invention.

Referring now to FIG. 3 for another preferred embodiment of the present invention, there is provided a pharmaceutical composition 1 comprising a core 2, a functional coating membrane 6 surrounding the core 2 and a top coating membrane 8 surrounding the functional coating membrane 6.

Figure 4:
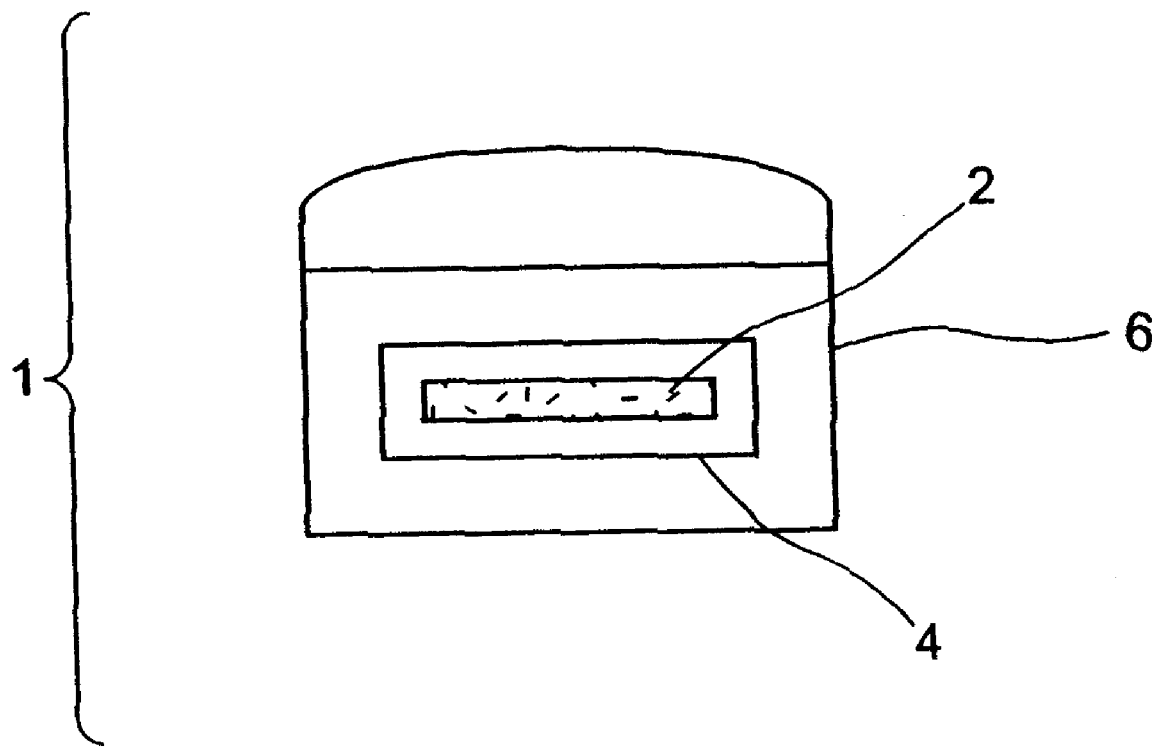
FIG. 4 is a perspective view of a vertical cross section of a pharmaceutical composition according to another embodiment of the present invention.

Referring now to FIG. 4 for another preferred embodiment of the present invention, there is provided a pharmaceutical composition 1 comprising a core 2, a seal coating membrane 4 surrounding the core 2, and a functional coating membrane 6 surrounding the seal coating membrane 4.

Figure 5:
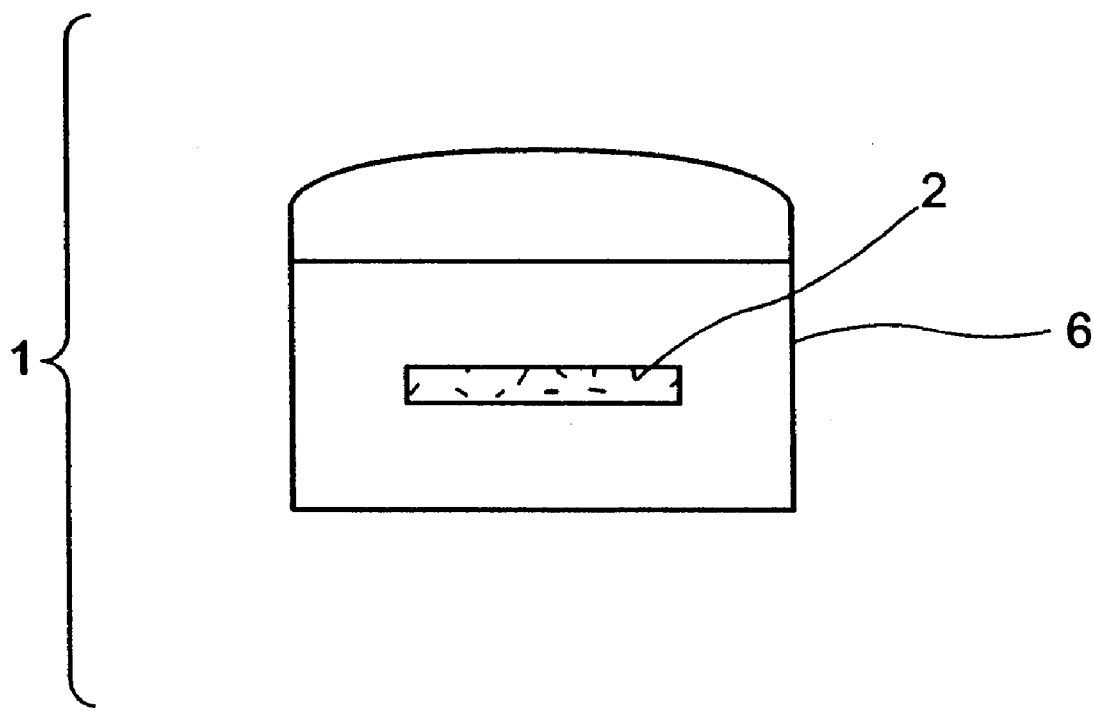
FIG. 5 is a perspective view of a vertical cross section of a pharmaceutical composition according to another embodiment of the present invention.

Referring now to FIG. 5 for another preferred embodiment of the present invention, there is provided a pharmaceutical composition 1 comprising a core 2 and a functional coating membrane 6 surrounding the core 2.

For the purpose of illustration, the following examples are presented which should not be considered as limiting to the scope of the present invention.

(a) EXAMPLE 1

A dosage form for delivering 11 mg of glipizide per tablet in a controlled and sustained rate may be manufactured as follows:

11.0 g of micronized glipizide was sieved through a #20 mesh sieve and blended with 200 g of E 50 premium Hydroxypropyl Methylcellulose. Then, the resulting blend was mixed with 175 g of Sodium Starch Glycolate. The resulting blend was then mixed with 48 g of Polyvinyl Pyrrolidone (K value 29 to 32). This blend was then granulated with a granulating solution containing Polyethylene Glycol 400 as a binder dissolved in Isopropyl alcohol (15% w/w). The resulting wet mass was dried at 60° C. for 3 hours. After drying, the granules were passed through a #20 mesh sieve to obtain the desired particle size. The granules obtained in the previous step were lubricated using 6 g of talc. These lubricated granules were compressed using a tablet press equipped with round tooling having a diameter of 0.4375" (Flat face beveled edge).

The uncoated tablets obtained above were coated using a perforated coating pan as explained below:

(I) Seal Coating Membrane: A seal coating membrane was applied on the surface of the uncoated tablets to achieve a weight gain of 1.66% W/W of the weight of the core. A 2% seal coating membrane is usually adequate for this purpose. The seal coating dispersion of Opadry® Clear (manufactured and marketed by Colorcon, Inc., PA) in water at a concentration of 10% W/W was sprayed onto the surface of the uncoated tablets using a perforated coating pan. Hydroxypropyl methylcellulose dispersion in water can also be used for this purpose.

(II) Functional Coating Membrane: A functional coating membrane consisting of an aqueous ethyl cellulose dispersion, a plasticizer, a film extender/diffusion enhancer and deionised water was applied to the seal coated tablets obtained from (I) above. In this particular example, the functional coating dispersion contained the following excipients at the following respective ratios:

| Ingredient | Concentration in dispersion* | Solids |
|---|---|---|
| Aquacoat ® ECD 30 (supplied at 30% solids) | 200.0 g | 60 g |
| HPMC E5 Prem. LV (as a 10% W/W dispersion) | 60.0 g | 6.0 g |
| Triethyl Citrate | 14.4 g | 14.4 g |
| Deionised Water | 261.6 g | 0.0 g |
| | 536.0 g | 80.4 g |

*Indicates the wt. of solution in dispersion.

This solution is sprayed onto the seal coated tablets using a perforated coating pan.

Alternatively any other aqueous ethyl cellulosic dispersion such as Surelease® and other grades of hydroxypropyl methylcellulose or other hydrophilic polymers may be used.

(III) Top Coating Membrane: A top coating membrane was applied to the surface of the functional coated tablets using a 10% W/W aqueous dispersion of Opadry® Clear to achieve a weight gain of 1.66% based on the weight of the uncoated tablets.

After the application of the seal coating membrane, the functional coating membrane and the top coating membrane, the tablets were cured at 60° C. for 1 hour and then allowed to cool. The weight gains obtained for the seal coating membrane, the functional coating membrane and the top coating membrane were 1.66%, 4.5% and 1.66% W/W of the weight of the core, respectively. All of the weight gains were calculated based on the weight of the uncoated tablets.

Figure 6:
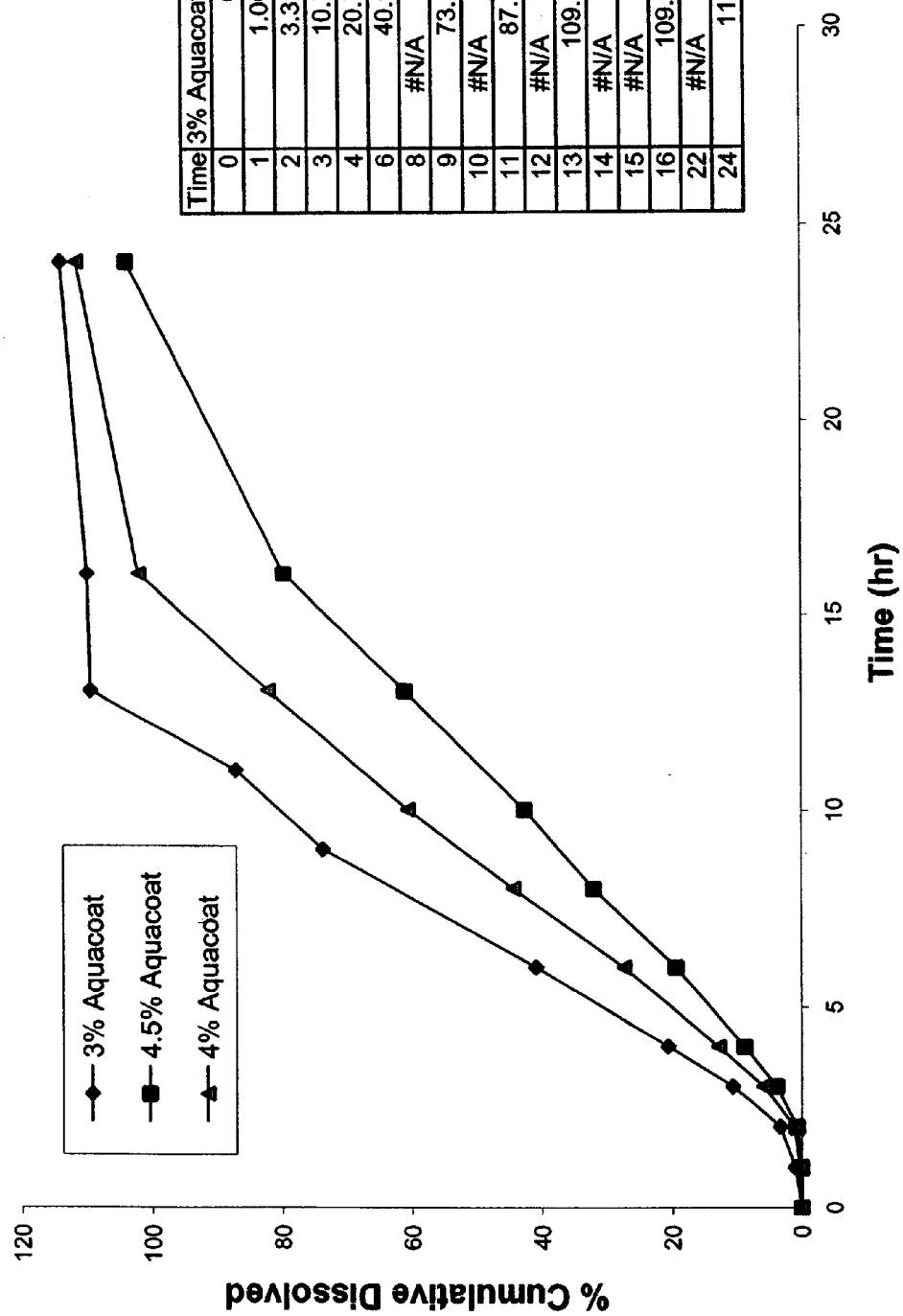
FIG. 6 is a graph illustrating the effect of varying the percent weight of the functional coating membrane on the release of the active ingredient glipizide from a pharmaceutical composition according to one embodiment of the present invention.

The weight gain of the functional coating membrane was varied from 3% to 4.5% W/W of the weight of the core. The effect of varying the weight gain of the functional coating membrane on the release of the active ingredient from the pharmaceutical composition is shown in FIG. 6. In this example, a two hour controlled onset (time delay) and a sustained release of the active ingredient for about 10 to 22 hours, post time delay was achieved.

The effect of varying the weight gain of the functional coating membrane on the release of glipizide from the pharmaceutical composition was determined using the sequentially pH change method. In this method, each tablet was exposed to 4 different pHs, beginning with pH 1.2 from 0–1 hr, pH 4.0 from 1–2 hr, pH 6.0 from 2–6 hr and pH 7.5 from 6–18 hr. The tablets were characterized by USP dissolution apparatus 2. The vessels were filled with 900 ml of dissolution medium at a paddle speed of 100 rpm at 37° C. A non-reactive wire was loosely coiled around each tablet to prevent from sticking to the glass and help it stay at the bottom of the vessel.

As can be concluded from FIG. 6, in this example, the greater the percentage weight of Aquacoat, the smaller the amount of drug dissolved per time.

(b) EXAMPLE 2

A dosage form for delivering 10 mg of glipizide per tablet in a controlled and sustained rate may be manufactured as follows:

10.0 g of micronized glipizide was sieved through a #20 mesh sieve and blended with 200 g of E 50 premium Hydroxypropyl Methylcellulose. Then, the resulting blend was mixed with 175 g of Sodium Starch Glycolate. The resulting blend was then mixed with 48 g of Polyvinyl Pyrrolidone (K value 29 to 32). This blend was then granulated with a granulating solution containing Polyethylene Glycol 400 as a binder dissolved in Isopropyl alcohol (15% w/w). The resulting wet mass was dried at 60° C. for 3 hours. After drying, the granules were passed through a #20 mesh sieve to obtain the desired particle size. The granules obtained in the previous step were lubricated using 6 g of talc. These lubricated granules were compressed using a tablet press equipped with round tooling having a diameter of 0.4375" (Flat face beveled edge).

The uncoated tablets obtained above were coated using a perforated coating pan as explained below:

(I) Seal Coating Membrane: A seal coating membrane was applied on the surface of the uncoated tablets to achieve a weight gain of 1.66% W/W of the weight of the core. A 2% seal coating membrane is usually adequate for this purpose. The seal coating dispersion of Opadry® Clear (manufactured and marketed by Colorcon, Inc., PA) in water at a concentration of 10% W/W was sprayed onto the surface of the uncoated tablets using a perforated coating pan. Hydroxypropyl methylcellulose dispersion in water can also be used for this purpose.

(II) Functional Coating Membrane: A functional coating membrane consisting of an aqueous ethyl cellulose dispersion, a plasticizer, a film extender/diffusion enhancer and deionised water was applied to the seal coated tablets obtained from (I) above. In this particular example, the functional coating dispersion contained the following excipients at the following respective ratios:

| Ingredient | Concentration in dispersion* | Solids |
|---|---|---|
| Aquacoat ® ECD 30 (supplied at 30% solids) | 200.0 g | 60 g |
| HPMC E5 Prem. LV (as a 10% W/W dispersion) | 60.0 g | 6.0 g |
| Triethyl Citrate | 14.4 g | 14.4 g |
| Deionised Water | 261.6 g | 0.0 g |
| | 536.0 g | 80.4 g |

*Indicates the wt. of solution in dispersion.

This solution is sprayed onto the seal coated tablets using a perforated coating pan.

Alternatively any other aqueous ethyl cellulosic dispersion such as Surelease® and other grades of hydroxypropyl methylcellulose or other hydrophilic polymers may be used.

(III) Top Coating Membrane: A top coating membrane was applied to the surface of the functional coated tablets using a 10% W/W aqueous dispersion of Opadry® Clear to achieve a weight gain of 1.66% W/W based on the weight of the uncoated tablets.

Figure 7:
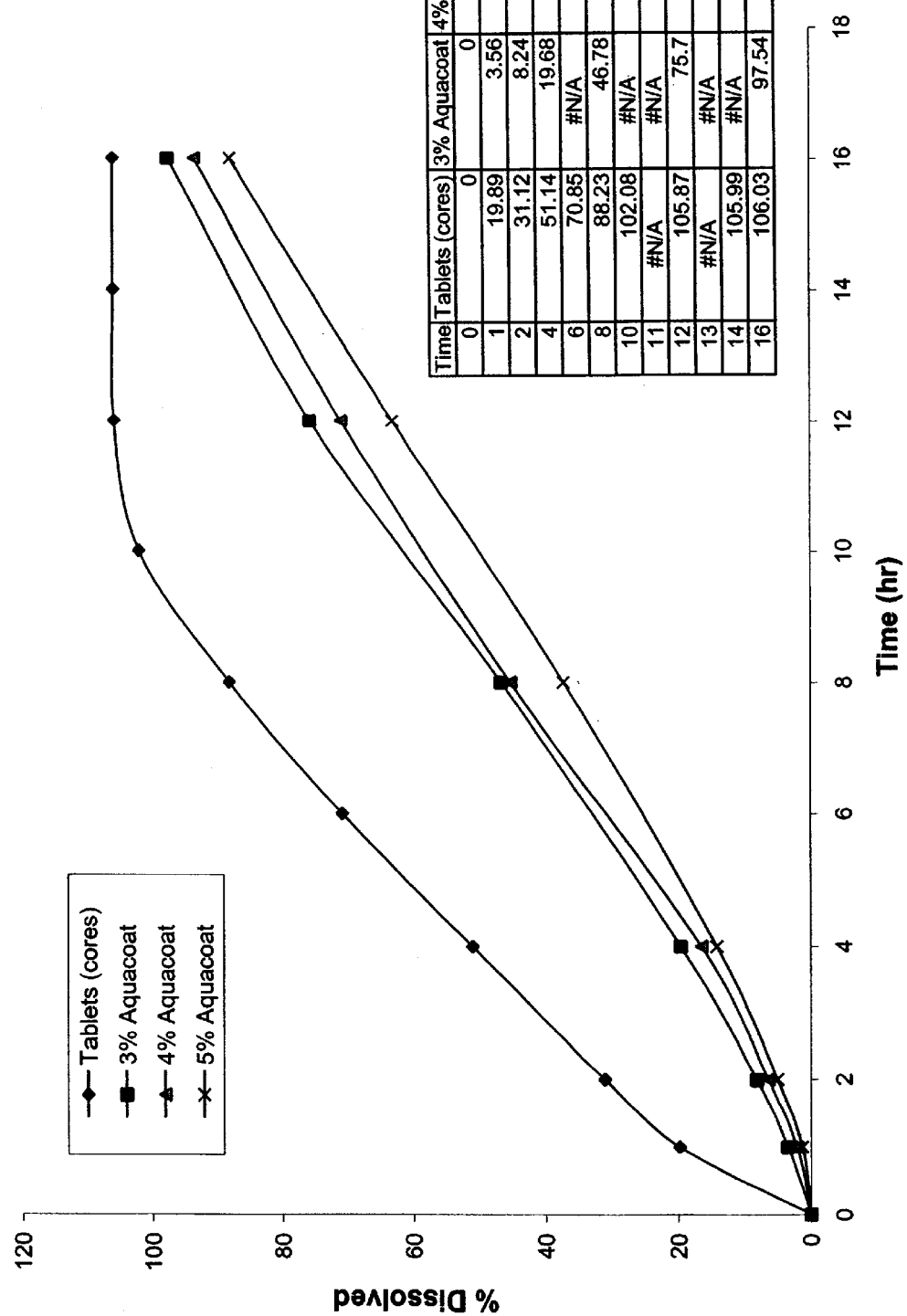
FIG. 7 is a graph illustrating the effect of varying the percent weight of the functional coating membrane on the release of the active ingredient glipizide from a pharmaceutical composition according to one embodiment of the present invention.

After the application of the seal coating membrane, the functional coating membrane and the top coating membrane, the tablets were cured at 60° C. for 1 hour and then allowed to cool. The weight gains obtained for the seal coating membrane, the functional coating membrane and the top coating membrane were 1.66%, 4.5% and 1.66% W/W of the weight of the core, respectively. All of the weight gains were calculated based on the weight of the uncoated tablets. The weight gain of the functional coating membrane was varied from 3% to 5.0% W/W of the weight of the core. The effect of varying the weight gain of the functional coating membrane on the release of the active ingredient from the pharmaceutical composition is shown in FIG. 7. In this example, a one hour controlled onset (time delay) and a sustained release of the active ingredient for about 8 to 16 hours, post time delay was achieved.

The effect of varying the weight gain of the functional coating membrane on the release of glipizide from the pharmaceutical composition was determined using the single pH method. In this method the pH of the dissolution medium was kept constant at pH 7.5. The tablets were characterized by USP dissolution apparatus 2. The vessels were filled with 900 ml of dissolution medium at a paddle speed of 100 rpm at 37° C. A non-reactive wire was loosely coiled around each tablet to prevent from sticking to the glass and help it stay at the bottom of the vessel.

As can be concluded from FIG. 7 in this example, there is no delay in the release of glipizide from the uncoated tablet, whereas for the tablets coated with Aquacoat, the release is delayed.

(c) EXAMPLE 3

A dosage form for delivering 240 mg of Verapamil per tablet in controlled and sustained rate may be manufactured as follows:

240 g of Verapamil HCl was sieved through a US#20 mesh sieve and blended with 150 g of E50 premium Hydroxypropyl Methylcellulose. To this blend was added 270.0 g croscarmellose sodium and mixed for 15 minutes. This blend was granulated with Polyvinyl Pyrrolidone K 29/32 solution in Isopropyl alcohol (30% w/w). The wet mass obtained in the above step was dried at 60° C. for 3 hours. After drying, the granules were passed through #20 mesh sieve. The granules were then mixed with 2.5 g of Magnesium Stearate and 15 g of Stearic acid in a V blender. This granule blend was compressed in a tablet press using appropriate size tooling.

These tablets were then coated using a perforated coating pan.

(I) Seal Coating Membrane: A seal coating membrane was applied on the surface of tablets to achieve a weight gain of 1.66% W/W of the weight of the core. A 2% seal coating membrane is usually adequate for this purpose. The seal coating dispersion of Opadry® Clear in water at a concentration of 10% W/W (manufactured and marketed by Colorcon, Inc., Pa.) was sprayed on to the surface of the tablets using a perforated coating pan. Alternatively, Hydroxypropyl methylcellulose dispersion with PEG 400 as plasticizer, in water can also be used for this purpose.

(II) Functional Coating Membrane: A functional coating membrane consisting of aqueous ethyl cellulose dispersion, a plasticizer, a film extender/diffusion enhancer and deionised water was applied to the seal coated tablets. In this particular example, the functional coating dispersion contained the following excipients at the following respective ratios.

| Ingredient | Concentration in dispersion* | Solids |
|---|---|---|
| Aquacoat ® ECD 30 (supplied at 30% solids) | 200.0 g | 60 g |
| HPMC E5 Prem. LV (as a 10% W/W dispersion) | 60.0 g | 6.0 g |
| Triethyl Citrate | 14.4 g | 14.4 g |
| Deionised Water | 261.6 g | 0.0 g |
| | 536.0 g | 80.4 g |

*Indicates the wt. of solution in dispersion.

This solution is sprayed onto the seal coated tablets using a perforated coating pan.

Alternatively any other aqueous ethyl cellulosic dispersion such as Surelease® and other grades of hydroxypropyl methyl cellulose or other hydrophilic polymers may be used.

(III) Top Coating Membrane: A top coating membrane is applied on top of the functional coating membrane using a 10% W/W aqueous dispersion of Opadry® Clear to achieve a weight gain of 1.66% W/W based on the weight of the uncoated tablets.

After the application of the seal coating membrane, the functional coating membrane and the top coating membrane, the tablets were cured at 60° C. for 1 hour and then allowed to cool.

The weight gains obtained for the seal coating membrane, the functional coating membrane and the top coating membrane are 1.66%, 4.5% and 1.66% W/W of the weight of the core, respectively.

The active ingredients used in the above examples are only used to illustrate the utility of the present invention. As mentioned previously, the present invention can be carried out using any desired active ingredient.

It will be appreciated that the present invention describes a method in which a drug could be given in a rate controlled manner with a proper time delay.

While the foregoing provides a detailed description of preferred embodiments of the invention, it is to be understood that it is intended that all material contained herein be interpreted as illustrative of the invention only and not in a limiting sense. Furthermore, numerous modifications, variations and adaptations may be made to the particular embodi- The embodiments of the invention in which an exclusive property or privilege is claimed are as follows:

1. A pharmaceutical composition for controlled onset and sustained release of an active ingredient, said composition comprising:
   (i) a core comprising:
      (a) an active ingredient;
      (b) a hydrophilic carrier;
      (c) a hydrodynamic diffusion enhancer; and optionally
      (d) conventional pharmaceutically acceptable excipients selected from the group consisting of binders, fillers and lubricants and combinations thereof; and
   (ii) a functional coating membrane surrounding said core, and optionally
   (iii) a seal coating membrane between the core and the functional coating membrane, and optionally
   (iv) a top coating membrane surrounding the functional coating membrane; wherein said composition provides a sustained release of the active ingredient from the composition for about 6 to about 24 hours.

2. A method for preparing a controlled onset sustained release pharmaceutical composition, said composition comprising:
   (i) a core comprising:
      (a) an active ingredient;
      (b) a hydrophilic carrier;
      (c) a hydrodynamic diffusion enhancer; and optionally
      (d) conventional pharmaceutically acceptable excipients selected from the group consisting of binders, fillers and lubricants;
   (ii) a functional coating membrane surrounding said core; and optionally;
   (iii) a seal coating membrane between the core and the functional coating membrane, and optionally;
   (iv) a top coating membrane surrounding the functional coating membrane;
   wherein the method comprises:
   (v) blending the active ingredient with the hydrophilic carrier, the hydrodynamic diffusion enhancer and optionally with the conventional pharmaceutically acceptable excipients;
   (vi) granulating the blend with a binder to obtain a wet mass;
   (vii) drying the wet mass at 60° C. for 3 hours;
   (viii) lubricating the granules with a lubricant;
   (ix) compressing the lubricated granules to form a core;
   (x) applying a functional coating membrane containing aqueous polymeric dispersions, with dispersed plasticizers, and film extenders/diffusion enhancers to the surface of the core; and
   (xi) curing of the coated core at a temperature range of 30° C.–80° C. for up to 12 hours; and optionally
   (xii) after forming the core, applying a seal coating membrane to the surface of the core to smooth out the surface; and optionally
   (xiii) after applying the functional coating membrane, applying a top coating membrane containing aqueous coating dispersions to the surface of the functional coating membrane.

3. A method for administering an active ingredient to a patient in need of therapy, which method comprises: administering a controlled onset sustained release pharmaceutical composition to the patient, said composition comprising:
   (i) a core comprising:
      (a) an active ingredient;
      (b) a hydrophilic carrier;
      (c) a hydrodynamic diffusion enhancer; and optionally
      (d) conventional pharmaceutically acceptable excipients selected from the group consisting of binders, fillers and lubricants and combinations thereof; and
   (ii) a functional coating membrane surrounding said core, and optionally
   (iii) a seal coating membrane between the core and the functional coating membrane, and optionally
   (iv) a top coating membrane surrounding the functional coating membrane; wherein said composition provides a sustained release of the active ingredient from the composition for about 6 to about 24 hours.

4. The pharmaceutical composition of claim 1 wherein the hydrophilic carrier is selected from the group consisting of heteropolysaccharides, xanthan gum, gellan gum, locust bean gum, propylene glycol ester, homopolysaccharides, galactomannan, glucomannan, guar gum, gum acacia, gum tragacanth, alkali metal carageenates, alginates, cellulose alkyl carboxylates, carboxymethyl cellulose, carboxyethyl cellulose, alkali metal salts of cellulose alkyl carboxylates, sodium carboxymethyl cellulose, carboxypolymethylene, hydroxypropyl methylcelluloses, hydroxypropyl cellulose, hydroxyethyl cellulose, hydroxyethyl methylcellulose, polyethylene glycols, polyethylene oxides, alginate salts, natural polysaccharides, gum arabica, and combinations thereof.

5. The pharmaceutical composition of claim 1 or 4 wherein the hydrophilic carrier is hydroxypropyl methylcellulose.

6. The pharmaceutical composition of claim 5 wherein the hydroxypropyl methylcellulose has a viscosity between about 5 cps and 100,000 cps, a hydroxypropoxyl content between about 7 and 12%, a methoxyl content between about 19 and 30%.

7. The pharmaceutical composition of claim 4 wherein the hydrophilic carrier is a blend of hydroxypropyl methylcelluloses having different molecular weights and/or viscosities.

8. The pharmaceutical composition of claim 7 wherein the ratio of the blend can vary from 1:99 to 99:1 with respect to low and higher molecular weight of hydroxypropyl methylcelluloses.

9. The pharmaceutical composition of claim 1 wherein the hydrophilic carrier in said core is present in a concentration of about 5 to 99% W/W of the weight of the core.

10. The pharmaceutical composition of claim 1 wherein the hydrodynamic diffusion enhancer is selected from the group consisting of sodium starch glycolate, sodium croscarmellose, gellan gum, starches, clays, celluloses, cellulose derivatives, alginates, crospovidone and combinations thereof.

11. The pharmaceutical composition of claim 1 wherein the hydrodynamic diffusion enhancer in said core is present in a concentration of about 5 to 60% W/W of the weight of the core.

12. The pharmaceutical composition of claim 1 wherein the binders in said core are present in a concentration of about 1 to 10% W/W of the weight of the core.

13. The pharmaceutical composition of claim 1 wherein the fillers and binders are each selected from the group consisting of polyethylene glycols, microcrystaline cellulose, lactose, starches, starch derivatives, mannitol, sorbitol, dextros, sucrose, maltodextrin, celluloses, cellulose derivatives, hydroxypropyl methylcellulose, hydroxypropyl ethylcellulose polyvinyl pyrrolidone, ethylcellulose, hydroxypropyl cellulose, hydroxyethyl cellulose, polysaccharides, gums, and combinations thereof.

14. The pharmaceutical composition of claim 1 wherein the fillers in said core are present in a concentration of about 2 to 4% W/W of the weight of the core.

15. The pharmaceutical composition of claim 1 wherein the lubricants and flow promoters are selected from the group consisting of stearic acid, talc, waxes, stearic acid salts, stearic acid derivatives, sodium stearyl fumarate, corn starch, silica derivatives and combinations thereof.

16. The pharmaceutical composition of claim 1 wherein the lubricants in said core are present in a concentration of about 0.25 to 4% W/W of the weight of the core.

17. The pharmaceutical composition of claim 1 wherein the functional coating membrane is an aqueous polymeric comprising dispersed plasticizers, film extenders and diffusion enhancers and wherein said aqueous polymeric dispersion is present in a concentration of about 1–25% W/W of the weight of the core.

18. The pharmaceutical composition of claim 1 wherein the ratio of the polymer to film extender in the aqueous polymeric dispersion is from about 0.25–0.75 to 0.99–0.01.

19. The pharmaceutical composition of claim 1 wherein the seal coating membrane is present in a concentration of about 0–5% W/W of the weight of the core.

20. The pharmaceutical composition of claim 1 wherein the top coating membrane is an aqueous coating dispersion, and wherein said aqueous coating dispersion is present in a concentration of about 0–5% W/W of the weight of the core.

21. The pharmaceutical composition of claim 20 wherein the aqueous coating dispersion further comprises dispersed colours.

22. The pharmaceutical composition of claim 1 wherein the release of the active ingredient from the pharmaceutical composition is delayed for about 30 minutes to about 6 hours after ingestion.

23. The pharmaceutical composition of claim 22 wherein the release of the active ingredient from the pharmaceutical composition is sustained for about 6 to about 24 hours after the predetermined time delay.

24. The pharmaceutical composition of claim 1 wherein the active ingredient is selected from the group consisting of
   (I) an anti-inflammatory drug selected from the group consisting of phenylbutazone, indomethacin, naproxen, ibuprofen, flurbiprofen, diclofenac, dexamethasone, oxaprozin, prednisone and prednisolone;
   (II) a coronary dilator drug selected from the group consisting of glyceryl trinitrate, isosorbide dinitrate and pentaerythritol tetranitrate;
   (III) a peripheral vasodilator drug selected from the group consisting of naftidrofuryl oxalate, cyclandelate and nicotinic acid;
   (IV) an anti-infective drug selected from the group consisting of erythromycin, cephalexin, naldixic acid, clarithromycin, cefuroxime, cefaclor, cefprozil, zidovudine, acyclovir, ofloxacin, ciprofloxacillin, azithromycin and flucloxacillin sodium;
   (V) a psychotropic and/or an antianxiety drug selected from the group consisting of fluazepam, diazepam, amitryptaline, doxepine, thioridazine, trifluperazine, fluphenazine, piperothiazine, haloperidol, maprotiline hydrochloride, imipremine, clorazepate, estazolam, lorazepam, alprazolam, bupropion, fluoxetine, buspirone, clonazepam, sertaline, zolpidem, desmethylimipramine, lithium carbonate, lithium sulfate and methylphenidate;
   (VI) a central stimulant drug selected from the group consisting of isoproterinol, amphetamine sulphate and amphetamine hydrochloride;
   (VII) an antihistamine drug selected from the group consisting of chlorpheniramine, bropheniramine, fexofenadine, loratidine and diphenhydramine;
   (VIII) a laxative and/or antidiarrheal drug selected from the group consisting of bisacodyl, magnesium hydroxide, loperamide, diphenoxylate, and dioctyl sodium sulfosuccinate;
   (IX) a decongestant drug selected from the group consisting of phenylpropanolamine and pseudoephedrine;
   (X) a vitamin substance selected from the group consisting of alphatocopherol, thiamin, pyridoxine and ascorbic acid;
   (XI) an antacid selected from the group consisting of aluminum trisilicate, aluminum hydroxide, cimetidine, ranitidine, famotidine, omeprazole and nizatidine;
   (XII) a gastrointestinal sedative selected from the group consisting of propantheline bromide and metoclorpramide;
   (XIII) a cerebral vasodilator selected from the group consisting of soloctidilum, naftidrofuryl oxalate, co-dergocrine mesylate, papaverine and pentoxifylline;
   (XIV) an anti-anginal drug selected from the group consisting of isosorbide dinitrate, pentaerythritol tetranitrate, verapamil, nifedipine, diltiazem, and glyceryl trinitrate;
   (XV) an antiarrythmic selected from the group consisting of verapamil, nifedipine, diltiazem, disopyramide, bretylium tosylate, quinidine sulfate, quinidine gluconate and procainamide;
   (XVI) an antihypertensive selected from the group consisting of methyldopa, captopril, hydralazine, propranolol, labetalol, sotalol, terazosin, enalapril, lisinopril, quinalapril, benazepril, ramipril, clonidine, fosinopril, felodipine, immodipine and amlodipine;
   (XVII) a vasoconstrictor selected from the group consisting of ergotamine;
   (XVIII) a substance which influences blood coagulability selected from the group consisting of protamine sulfate and epsilon aminocaproic acid;
   (XIX) a hypnotic selected from the group consisting of dichloral phenazone, nitrazepam and temazepam;
   (XX) an antinauseant selected from the group consisting of chlorpromazine and promethazine theoclate;
   (XXI) an anticonvulsant selected from the group consisting of sodium valproate, phenytoin sodium, divalproex sodium and carbamezipine;
   (XXII) a neuromuscular drug selected from the group consisting of dentrolene sodium;
   (XXIII) a hypoglycemic agent selected from the group consisting of diabenese, insulin, glyburide, glipizide and troglitazone;
   (XXIV) a drug used in treating thyroid gland disorders, selected from the group consisting of thyroxin, triiodothyronine and propylthiouracil;
   (XXV) a diuretic selected from the group consisting of furosemide, chlorthalidone, hydrochlorthiazide, spironolactone, triampterene and indapamide;

(XXVI) a uterine relaxant medication selected from the group consisting of ritodrine;

(XXVII) an appetite suppressant selected from the group consisting of asphenteramine, diethylproprion hydrochloride and fenfluramine hydrochloride;

(XXVIII) an erythropoietic substance selected from group consisting of folic acid, calcium gluconate and ferrous sulphate;

(XXIX) an antiasthmatic drug selected from the group consisting of aminophylline, theophylline, orciprenaline sulphate, terbutaline sulphate, albuterol and salbutamol;

(XXX) an expectorant selected from the group consisting of carbocisteine and guaiphenesin;

(XXXI) a cough suppressant selected from the group consisting of noscapine, codeine phosphate, codeine sulfate, oxycodone, dihydrocodeine tartrate, oxycodeinone and dextromethorphan;

(XXXII) an antiuricemic drug selected from the group consisting of allopurinol, probenecid and sulphinpyrazone;

(XXXIII) an antiseptic selected from the group consisting of cetylpyridinium chloride, tyrothricin and chlorhexidine;

(XXXIV) an antilipidimic or anticholesterol agent selected from the group consisting of lovastatin, gemfibrozil, simvastatin and pravastatin; and pharmaceutically acceptable salts thereof.

25. A method for producing a delay of from about 30 minutes to about 6 hours in the onset of release of an active ingredient from a pharmaceutical composition in a patient in need of therapy, wherein the method comprises:
(A) administering a controlled onset sustained release pharmaceutical composition to the patient, said composition comprising:
 (i) a core comprising:
  (a) an active ingredient;
  (b) a hydrophilic carrier;
  (c) a hydrodynamic diffusion enhancer; and optionally
  (d) conventional pharmaceutically acceptable excipients selected from the group consisting of binders, fillers and lubricants and combinations thereof; and
 (ii) a functional coating membrane surrounding said core, and optionally
 (iii) a seal coating membrane between the core and the functional coating membrane, and optionally
 (iv) a top coating membrane surrounding the functional coating membrane.

26. The method of claim 2, 3 or 25 wherein the seal coating membrane is present in a concentration of about 0–5% W/W of the weight of the core.

27. The method of claim 2, 3 or 25 wherein the top coating membrane is an aqueous coating dispersion, and wherein said aqueous coating dispersion is present in a concentration of about 0–5% W/W of the weight of the core.

28. The method of claim 27 wherein the aqueous coating dispersion further comprises dispersed colours.

29. The method of claim 2, 3 or 25 wherein the release of the active ingredient from the pharmaceutical composition is delayed for about 30 minutes to about 6 hours after ingestion.

30. The method of claim 2, 3 or 25 wherein the release of the active ingredient from the pharmaceutical composition is sustained for about 6 to about 24 hours after the predetermined time delay.

31. The method of claim 25, 28, or 29 wherein the active ingredient is selected from the group consisting of
(I) an anti-inflammatory drug selected from the group consisting of phenylbutazone, indomethacin, naproxen, ibuprofen, flurbiprofen, diclofenac, dexamethasone, oxaprozin, prednisone and prednisolone;
(II) a coronary dilator drug selected from the group consisting of glyceryl trinitrate, isosorbide dinitrate and pentaerythritol tetranitrate;
(III) a peripheral vasodilator drug selected from the group consisting of naftidrofuryl oxalate, cyclandelate and nicotinic acid;
(IV) an anti-infective drug selected from the group consisting of erythromycin, cephalexin, naldixic acid, clarithromycin, cefuroxime, cefaclor, cefprozil, zidovudine, acyclovir, ofloxacin, ciprofloxacillin, azithromycin and flucloxacillin sodium;
(V) a psychotropic and/or an antianxiety drug selected from the group consisting of fluazepam, diazepam, amitryptaline, doxepine, thioridazine, trifluperazine, fluphenazine, piperothiazine, haloperidol, maprotiline hydrochloride, imipremine, clorazepate, estazolam, lorazepam, alprazolam, bupropion, fluoxetine, buspirone, clonazepam, sertaline, zolpidem, desmethylimipramine, lithium carbonate, lithium sulfate and methylphenidate;
(VI) a central stimulant drug selected from the group consisting of isoproterinol, amphetamine sulphate and amphetamine hydrochloride;
(VII) an antihistamine drug selected from the group consisting of chlorpheniramine, bropheniramine, fexofenadine, loratidine and diphenhydramine;
(VIII) a laxative and/or antidiarrheal drug selected from the group consisting of bisacodyl, magnesium hydroxide, loperamide, diphenoxylate, and dioctyl sodium sulfosuccinate;
(IX) a decongestant drug selected from the group consisting of phenylpropanolamine and pseudoephedrine;
(X) a vitamin substance selected from the group consisting of alphatocopherol, thiamin, pyridoxine and ascorbic acid;
(XI) an antacid selected from the group consisting of aluminum trisilicate, aluminum hydroxide, cimetidine, ranitidine, famotidine, omeprazole and nizatidine;
(XII) a gastrointestinal sedative selected from the group consisting of propantheline bromide and metoclorpramide;
(XIII) a cerebral vasodilator selected from the group consisting of soloctidilum, naftidrofuryl oxalate, co-dergocrine mesylate, papaverine and pentoxifylline;
(XIV) an anti-anginal drug selected from the group consisting of isosorbide dinitrate, pentaerythritol tetranitrate, verapamil, nifedipine, diltiazem, and glyceryl trinitrate;
(XV) an antiarrythmic selected from the group consisting of verapamil, nifedipine, diltiazem, disopyramide, bretylium tosylate, quinidine sulfate, quinidine gluconate and procainamide;
(XVI) an antihypertensive selected from the group consisting of methyldopa, captopril, hydralazine, propranolol, labetalol, sotalol, terazosin, enalapril, lisinopril, quinalapril, benazepril, ramipril, clonidine, fosinopril, felodipine, immodipine and amlodipine;
(XVII) a vasoconstrictor selected from the group consisting of ergotamine;

(XVIII) a substance which influences blood coagulability selected from the group consisting of protamine sulfate and epsilon aminocaproic acid;

(XIX) a hypnotic selected from the group consisting of dichloral phenazone, nitrazepam and temazepam;

(XX) an antinauseant selected from the group consisting of chlorpromazine and promethazine theoclate;

(XXI) an anticonvulsant selected from the group consisting of sodium valproate, phenytoin sodium, divalproex sodium and carbamezipine;

(XXII) a neuromuscular drug selected from the group consisting of dentrolene sodium;

(XXIII) a hypoglycemic agent selected from the group consisting of diabenese, insulin, glyburide, glipizide and troglitazone;

(XXIV) a drug used in treating thyroid gland disorders, selected from the group consisting of thyroxin, triiodothyronine and propylthiouracil;

(XXV) a diuretic selected from the group consisting of furosemide, chlorthalidone, hydrochlorthiazide, spironolactone, triampterene and indapamide;

(XXVI) a uterine relaxant medication selected from the group consisting of ritodrine;

(XXVII) an appetite suppressant selected from the group consisting of asphenteramine, diethylproprion hydrochloride and fenfluramine hydrochloride;

(XXVIII) an erythropoietic substance selected from group consisting of folic acid, calcium gluconate and ferrous sulphate;

(XXIX) an antiasthmatic drug selected from the group consisting of aminophylline, theophylline, orciprenaline sulphate, terbutaline sulphate, albuterol and salbutamol;

(XXX) an expectorant selected from the group consisting of carbocisteine and guaiphenesin;

(XXXI) a cough suppressant selected from the group consisting of noscapine, codeine phosphate, codeine sulfate, oxycodone, dihydrocodeine tartrate, oxycodeinone and dextromethorphan;

(XXXII) an antiuricemic drug selected from the group consisting of allopurinol, probenecid and sulphinpyrazone;

(XXXIII) an antiseptic selected from the group consisting of cetylpyridinium chloride, tyrothricin and chlorhexidine;

(XXXIV) an antilipidimic or anticholesterol agent selected from the group consisting of lovastatin, gemfibrozil, simvastatin and pravastatin; and pharmaceutically acceptable salts thereof.

32. The method of claim 2, 28 or 29 wherein the hydrophilic carrier is selected from the group consisting of heteropolysaccharides, xanthan gum, locust bean gum, propylene glycol ester, homopolysaccharides, galactomannan, glucomannan, guar gum, gum acacia, gum tragacanth, alkali metal carageenates, alginates, cellulose alkyl carboxylates, carboxymethyl cellulose, carboxyethyl cellulose, alkali metal salts of cellulose alkyl carboxylates, sodium carboxymethyl cellulose, carboxypolymethylene, hydroxypropyl methylcelluloses, hydroxypropyl cellulose, hydroxyethyl cellulose, hydroxyethyl methylcellulose, polyethylene glycols, polyethylene oxides, alginate salts, natural polysaccharides, gum arabica and combinations thereof.

33. The method of claim 32 wherein the hydrophilic carrier is hydroxypropyl methylcellulose.

34. The method of claim 33 wherein the hydroxypropyl methylcellulose has a viscosity between about 5 cps and 100,000 cps, a hydroxypropoxyl content between about 7 and 12%, a methoxyl content between about 19 an d 30%.

35. The method of claim 32 wherein the hydrophilic carrier is a blend of hydroxypropyl methylcelluloses having different molecular weights and/or viscosities.

36. The method of claim 35 wherein the ratio of the blend can vary from 1:99 to 99:1 with respect to low and higher molecular weight of hydroxypropyl methylcelluloses.

37. The method of claim 25, 28 or 29 wherein the hydrophilic carrier in said core is present in a concentration of about 5 to 99% W/W of the weight of the core.

38. The method of claim 25, 28 or 29 wherein the hydrodynamic diffusion enhancer is selected from the group consisting of sodium starch glycolate, sodium croscarmellose, gellan gum, crospovidone, starches, clays, celluloses, cellulose derivatives, alginates and combinations thereof.

39. The method of claim 25, 28 or 29 wherein the hydrodynamic diffusion enhancer in said core is present in a concentration of about 5 to 60% W/W of the weight of the core.

40. The method of claim 25, 28 or 29 wherein the binders in said core are present in a concentration of about 1 to 10% W/W of the weight of the core.

41. The method of claim 2, 3 or 25 wherein the fillers and binders are each selected from the group consisting of polyethylene glycols, microcrystalline cellulose, lactose, starches, starch derivatives, mannitol, sorbitol, dextrose, sucrose, maltodextrin, celluloses, cellulose derivatives, hydroxypropyl methylcellulose, hydroxypropyl ethylcellulose, polyvinyl pyrrolidone, ethyl cellulose, hydroxypropyl cellulose, hydroxyethyl cellulose, polysaccharides, gums, and combinations thereof.

42. The method of claim 25, 28 or 29 wherein the fillers in said core are present in a concentration of about 2 to 40% W/W of the weight of the core.

43. The method of claim 25, 28 or 29 wherein the lubricants and flow promoters are selected from the group consisting of stearic acid, talc, waxes, stearic acid salts, stearic acid derivatives, sodium stearyl fumarate, corn starch, silica derivatives and combinations thereof.

44. The method of claim 25, 28 or 29 wherein the lubricants in said core are present in a concentration of about 0.25 to 4% W/W of the weight of the core.

45. The method of claim 25, 28 or 29 wherein the functional coating membrane is an aqueous polymeric dispersion comprising dispersed plasticizers, film extenders and diffusion enhancers and wherein said aqueous polymeric dispersion is present in a concentration of about 1–25% W/W of the weight of the core.

46. The method of claim 45 wherein the ratio of the polymer to film extender in the aqueous polymeric dispersion is from about 0.25–0.75 to 0.99–0.01.

* * * * *